United States Patent
Venugopal et al.

(10) Patent No.: US 10,674,986 B2
(45) Date of Patent: Jun. 9, 2020

(54) METHODS FOR PERSONALIZING BLOOD FLOW MODELS

(71) Applicant: General Electric Company, Schenectady, NY (US)

(72) Inventors: Prem Venugopal, Clifton Park, NY (US); Jed Douglas Pack, Glenville, NY (US); Bruno Kristiaan Bernard De Man, Clifton Park, NY (US); Peter Michael Edic, Albany, NY (US); Jiang Hsieh, Brookfield, WI (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 708 days.

(21) Appl. No.: 15/154,360

(22) Filed: May 13, 2016

(65) Prior Publication Data
US 2017/0325769 A1 Nov. 16, 2017

(51) Int. Cl.
*A61B 6/00* (2006.01)
*A61B 6/03* (2006.01)

(52) U.S. Cl.
CPC ............ *A61B 6/5217* (2013.01); *A61B 6/032* (2013.01); *A61B 6/40* (2013.01); *A61B 6/481* (2013.01); *A61B 6/503* (2013.01); *A61B 6/504* (2013.01); *A61B 6/5205* (2013.01)

(58) Field of Classification Search
CPC ........ A61B 6/5217; A61B 6/504; A61B 6/481
See application file for complete search history.

(56) References Cited

U.S. PATENT DOCUMENTS

| | | |
|---|---|---|
| 4,716,904 A | 1/1988 | Meno |
| 7,603,154 B2 | 10/2009 | Noble et al. |
| 8,157,742 B2 | 4/2012 | Taylor |
| 8,249,815 B2 | 8/2012 | Taylor |
| 8,311,747 B2 | 11/2012 | Taylor |
| 8,311,748 B2 | 11/2012 | Taylor et al. |
| 8,311,750 B2 | 11/2012 | Taylor |
| 8,315,812 B2 | 11/2012 | Taylor |
| 8,315,813 B2 | 11/2012 | Taylor et al. |
| 8,315,814 B2 | 11/2012 | Taylor et al. |
| 8,321,150 B2 | 11/2012 | Taylor |
| 8,386,188 B2 | 2/2013 | Taylor et al. |
| 8,496,594 B2 | 7/2013 | Taylor et al. |
| 8,523,779 B2 | 7/2013 | Taylor et al. |

(Continued)

OTHER PUBLICATIONS

Vander Horst et al. (Computational aand Mathematical Methods in Medicine vol. 2013, Article ID 393792, 15 pgs, 2013 (Year: 2013).*

(Continued)

*Primary Examiner* — Joseph M Santos Rodriguez
(74) *Attorney, Agent, or Firm* — Fletcher Yoder, P.C.

(57) ABSTRACT

The present approach provides a non-invasive methodology for estimation of coronary flow and/or fractional flow reserve. In certain implementations, various approaches for personalizing blood flow models of the coronary vasculature are described. The described personalization approaches involve patient-specific measurements and do not assume or rely on the resting coronary flow being proportional to myocardial mass. Consequently, there are fewer limitations in using these approaches to obtain coronary flow and/or fractional flow reserve estimates non-invasively.

14 Claims, 12 Drawing Sheets

(56) References Cited

U.S. PATENT DOCUMENTS

| | | | |
|---|---|---|---|
| 8,548,778 | B1 | 9/2013 | Taylor et al. |
| 8,594,950 | B2 | 10/2013 | Hart et al. |
| 8,606,530 | B2 | 11/2013 | Taylor |
| 8,630,812 | B2 | 1/2014 | Taylor |
| 8,706,457 | B2 | 4/2014 | Hart et al. |
| 8,734,356 | B2 | 5/2014 | Taylor |
| 8,734,357 | B2 | 5/2014 | Taylor |
| 8,768,669 | B1 | 7/2014 | Hart et al. |
| 8,768,670 | B1 | 7/2014 | Hart et al. |
| 8,812,245 | B2 | 8/2014 | Taylor |
| 8,812,246 | B2 | 8/2014 | Taylor |
| 8,824,752 | B1 | 9/2014 | Fonte et al. |
| 8,831,314 | B1 | 9/2014 | Fonte et al. |
| 8,831,315 | B1 | 9/2014 | Fonte et al. |
| 8,837,860 | B1 | 9/2014 | Grady et al. |
| 8,855,984 | B2 | 10/2014 | Hart et al. |
| 8,861,820 | B2 | 10/2014 | Fonte et al. |
| 9,135,699 | B2 | 9/2015 | Ralovich et al. |
| 2008/0167552 | A1* | 7/2008 | Bouchevreau ......... A61B 6/481 600/431 |
| 2008/0319309 | A1* | 12/2008 | Bredno ................ A61B 5/0275 600/420 |
| 2010/0259550 | A1* | 10/2010 | Baumgart ............. A61B 6/463 345/589 |
| 2013/0172734 | A1 | 7/2013 | Hsieh |
| 2013/0226003 | A1 | 8/2013 | Edic et al. |
| 2013/0243294 | A1 | 9/2013 | Ralovich et al. |
| 2013/0246034 | A1 | 9/2013 | Sharma et al. |
| 2014/0005535 | A1 | 1/2014 | Edic et al. |
| 2014/0088414 | A1 | 3/2014 | Mittal et al. |
| 2014/0270427 | A1* | 9/2014 | Fonte ................... G06T 7/0012 382/128 |
| 2015/0065864 | A1 | 3/2015 | Sharma et al. |
| 2015/0317429 | A1 | 11/2015 | Peters et al. |
| 2015/0324962 | A1 | 11/2015 | Itu et al. |
| 2015/0324965 | A1 | 11/2015 | Itu et al. |
| 2017/0325769 | A1* | 11/2017 | Venugopal ........... A61B 6/5217 |
| 2017/0325770 | A1 | 11/2017 | Edic et al. |

OTHER PUBLICATIONS

Boutsianis, E., et al., "Computational simulation of intracoronary flow based on real coronary geometry," European journal of Cardiothoracic Surgery , vol. 26, Issue 2, pp. 248-256 (2004).

Chang, WT., et al., "Ultrasound Based Assessment of Coronary Artery Flow and Coronary Flow Reserve Using the Pressure Overload Model in Mice," Journal of Visualized Experiments, Issue 98, e52598, (Apr. 2015) (Abstract).

Feldman, CL., et al., "Determination of in vivo velocity and endothelial shear stress patterns with phasic flow in human coronary arteries: a methodology to predict progression of coronary atherosclerosis," American Heart Journal, vol. 143, Issue 6, pp. 931-939 (Jun. 2002) (Abstract).

Frauenfelder, T., et al., "In-vivo flow simulation in coronary arteries based on computed tomography datasets: feasibility and initial results," European Radiology, vol. 17, Issue 5, pp. 1291-1300 (2007).

Huo, Y. and Kassab, G.S., "A hybrid one-dimensional/Womersley model of pulsatile blood flow in the entire coronary arterial tree," American Journal of Physiology—Heart and Circulatory Physiology, vol. 292, Issue 6, pp. H2623-H2633 (Jan. 2007).

Ilegbusi, OJ., et al., "Determination of blood flow and endothelial shear stress in human coronary artery in vivo," The Journal of invasive cardiology, vol. 11, Issue 11, pp. 667-674 (1999) (Abstract).

Krams, R., et al., "Evaluation of endothelial shear stress and 3D geometry as factors determining the development of atherosclerosis and remodeling in human coronary arteries in vivo, Combining 3D reconstruction from angiography and ivus (ANGUS) with computational fluid dynamics," Arteriosclerosis Thrombosis and Vascular Biology, vol. 17, Issue 10, pp. 2061-2065 (1997) (Abstract).

Myers, J. G., et al., "Factors influencing blood flow patterns in the human right coronary artery," Annals of biomedical engineering, vol. 29, Issue 2, pp. 109-120 (Feb. 2001) (Abstract).

Olufsen, M. et al., "Numerical simulation and experimental validation of blood flow in arteries with structured-tree outflow conditions," Annals of biomedical engineering, vol. 28, Issue 11, pp. 1281-1299 (Nov. 2000).

Reymond, P., et al., "Validation of a one-dimensional model of the systemic arterial tree," AJP Heart and Circulatory Physiology, vol. 297, Issue 1, pp. H208-H222 (2009).

Senzaki, H, et al., "Single-beat estimation of end-systolic pressure-volume relation in humans. A new method with the potential for noninvasive application," Circulation, vol. 94, Issue 10, pp. 2497-2506 (1996) (Abstract).

Smith, N. P., et al., "An anatomically based model of transient coronary blood flow in the heart," SIAM Journal on Applied mathematics, vol. 62, Issue 3, pp. 990-1018 (2002).

Segers, P., et al., "Systemic and pulmonary hemodynamics assessed with a lumped-parameter heart-arterial interaction model," Journal of Engineering Mathematics, vol. 47, Issue 3-4, pp. 185-199 (Dec. 2003).

Taylor, C.A.; et al.; "Patient-Specific Modeling of Cardiovascular Mechanics", Annual Review of Biomedical Engineering, vol. 11, pp. 109-134, 2009.

Troebs, Monique, et al.; "Estimation of Fractional Flow Reserve Based on Fluid Dynamic Modeling Using Coronary Angiographic Lesion Morphology-Accuracy Compared to Invasively Measured FFR", Journal of the American College of Cardiology, vol. 65, Issue 10, pp. A1068, Mar. 2015.

\* cited by examiner

Position in vessel (cm)

Position in vessel (cm)

METHODS FOR PERSONALIZING BLOOD FLOW MODELS

BACKGROUND

The subject matter disclosed herein relates to estimation of coronary flow and fractional flow reserve using imaging techniques.

Non-invasive imaging technologies allow images of the internal structures or features of a patient to be obtained without performing an invasive procedure on the patient. In particular, such non-invasive imaging technologies rely on various physical principles, such as the differential transmission of X-rays through the target volume or the reflection of acoustic waves, to acquire data and to construct images or otherwise represent the observed internal features of the patient.

For example, computed tomography (CT), including coronary computed tomography angiography (CCTA) devices and techniques, is an imaging technology based on the observed transmission of X-rays through the patient for a range of angular positions that is sufficient for image reconstruction. With the introduction of multi-slice CT scanners and faster rotation speeds, it has become possible to generate useful images of the heart. By way of example, computed tomography can accurately determine the reduction in lumen diameter due to a coronary artery stenosis (i.e., a narrowing of the coronary vessel, such as due to atherosclerotic plaque). However, anatomic presence or identification of a stenosis does not necessarily translate to actual functional significance, i.e. oxygen deprivation to myocardial tissue, to the patient.

With this in mind, the concept of fractional flow reserve was introduced to address this issue. Fractional flow reserve is the ratio of pressure distal to the stenosis to the pressure proximal to it and measures the hemodynamic resistance of the stenosis relative to the resistance of the coronary microcirculation. In conventional approaches, fractional flow reserve is measured at the time of invasive angiography by inserting a tiny guide wire through a standard diagnostic catheter. A sensor at the tip of the wire measures pressure. Pressure is measured both distal and proximal to the stenosis in the coronary artery to estimate fractional flow reserve. Such approaches, however, may be undesirable due to their invasive nature.

BRIEF DESCRIPTION

In one implementation, a method for generating a patient-specific coronary flow model is provided. In accordance with this method, contrast-enhanced images of a coronary vasculature at one or more cardiac phases are acquired or generated. The contrast-enhanced images are analyzed to determine spatial contrast agent concentration distribution in each vessel segment of interest. A generalized coronary model that models a coronary vasculature comprising at least each vessel segment of interest is accessed. The generalized coronary model is parameterized by one or more parameters. The one or more parameters of the generalized coronary model are tuned to generate a patient-specific coronary flow model that replicates the spatial contrast agent concentration distribution in each vessel segment of interest as observed in the contrast-enhanced images.

In a further implementation, an X-ray based imaging system is provided. In accordance with this implementation, the X-ray based imaging system includes: an X-ray source and X-ray detector configured to generate X-ray attenuation data for an imaging volume at a plurality of view angles about the imaging volume; and a processing component configured to receive raw or processed data read out from the X-ray detector. The processing component is configured to: acquire or generate contrast-enhanced images of a coronary vasculature at one or more cardiac phases, wherein the coronary vasculature comprises one or more vessel segments of interest; analyze the contrast-enhanced images to determine spatial contrast agent concentration distribution in each vessel segment of interest; and tune one or more parameters of a generalized coronary model to generate a tuned coronary flow model that replicates the spatial contrast agent concentration distribution in each vessel segment of interest as observed in the contrast-enhanced images.

In another implementation, a non-transitory, computer-readable medium is provided. The non-transitory, computer-readable medium stores routines that, when executed by a processor, cause acts to be performed comprising: acquiring or generating contrast-enhanced images of a coronary vasculature at one or more cardiac phases, wherein the coronary vasculature comprises one or more vessel segments of interest; analyzing the contrast-enhanced images to determine spatial contrast agent concentration distribution in each vessel segment of interest; and tuning one or more parameters of a generalized coronary model to generate a tuned coronary flow model that replicates the spatial contrast agent concentration distribution in each vessel segment of interest as observed in the contrast-enhanced images.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
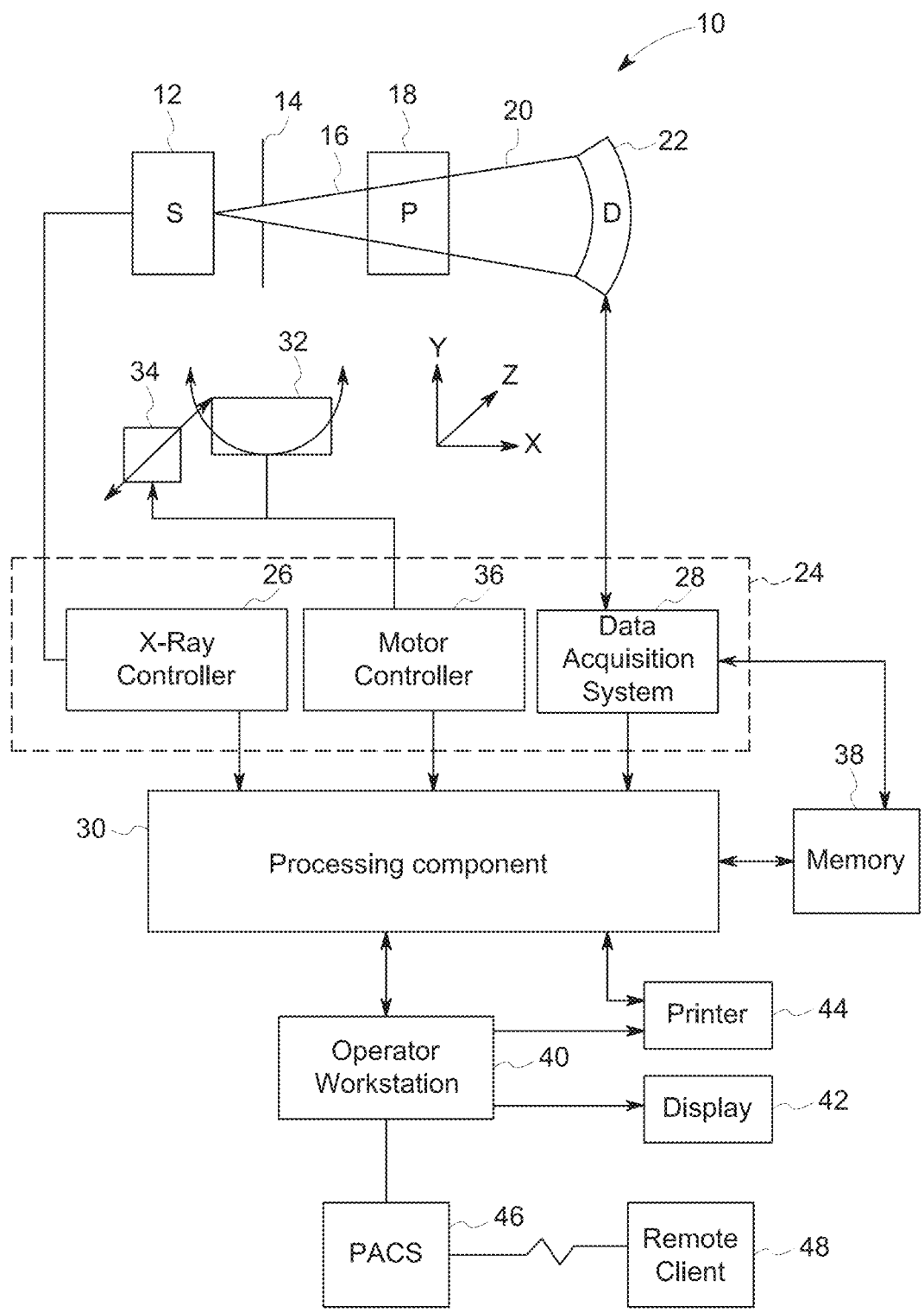
FIG. 1 is a block diagram depicting components of a computed tomography (CT) imaging system, in accordance with aspects of the present disclosure.

Development of a non-invasive method to assess coronary anatomy, including coronary flow and fractional flow reserve, may be a useful tool in providing cardiac healthcare. Such a non-invasive approach may reduce patient risks due to the reduction or elimination of certain interventional procedures as well as reducing healthcare costs for cardiac care. In some approaches, fractional flow reserve can be obtained non-invasively in the coronary arteries by combining Computational Fluid Dynamics (CFD) tools with a model of the coronary vasculature constructed from medical images. Prior three-dimensional (3D) CFD studies of the coronary arteries included calculations done using single 3D coronary vessel segments, constructed from intravascular ultrasound images or computed tomography angiography (CTA) images, as well as 3D coronary tree models constructed from CTA images. One-dimensional (1D) models have also have been used to simulate blood flow and pressure in the coronary tree. However, patient-specific boundary conditions were not used in these calculations.

Recently, some studies have extended these approaches to impose patient-specific boundary conditions. One aspect of certain of these models in imposing these patient-specific boundary conditions is the assumption of resting coronary flow being proportional to a measure myocardial mass determined from medical images. This, along with assumptions that the coronary microcirculation resistance is inversely proportional to cube of the diameter of the terminal vessels effectively determines flow in the coronary tree vessel segments. While such approaches have shown promising results, the assumptions involved limit their applicability to the population with coronary artery disease. For example, the assumption of coronary flow being proportional to myocardial mass is not valid for patients with rest angina.

With the preceding in mind the present approach provides a non-invasive methodology for estimation of coronary flow and/or fractional flow reserve without these limitations, such as without relying on the myocardial mass. In certain implementations discussed below, various approaches for personalizing blood flow models of the coronary vasculature are described. The described approaches involve patient-specific measurements and do not assume or rely on the resting coronary flow being proportional to myocardial mass, as in prior approaches. Consequently, there are fewer limitations in using these approaches to obtain fractional flow reserve estimates non-invasively. As discussed below, disclosed approaches include: approaches based on contrast dynamics (discussed in Section 1), approaches based on cardiac dynamics (discussed in Section 2), approaches based on coronary vessel dynamics (discussed in Section 3), and approaches based on ultrasound (discussed in Section 4).

With the foregoing in mind, it may be useful to provide a brief description of basic components of a CT system that may be used in accordance with the present disclosure. For example, turning to FIG. 1, a CT imaging system 10 is depicted that may be used to acquire X-ray attenuation data at a variety of view angle positions as the gantry rotates around a patient; these data would be suitable for CCTA. In the embodiment illustrated in FIG. 1, imaging system 10 includes a source of X-ray radiation 12 positioned adjacent to a collimator, beam-shaper, or beam-limiter 14. The X-ray source 12 may be an X-ray tube, a distributed X-ray source (such as an X-ray source with solid-state or thermionic electron emission) or any other source of X-ray radiation suitable for the acquisition of medical or other images.

The beam-shaper 14 permits X-rays 16 to pass into a region in which a patient 18, is positioned. In the depicted example, the X-rays 16 are collimated to a cone-shaped beam and/or a fan-shaped beam that passes through the imaged volume. A portion of the X-ray radiation 20 passes through or around the patient 18 (or other subject of interest) and impacts a detector array, such as a multi-slice or flat-panel digital detector, represented generally as reference numeral 22. Detector elements of the array produce electrical signals that represent the intensity of the incident X-rays 20. These signals are acquired and processed to reconstruct images of the features within the patient 18.

Source 12 is controlled by a system controller 24, which furnishes both power, and control signals for CCTA examination sequences. In the depicted embodiment, the system controller 24 controls the source 12 via an X-ray controller 26 which may be a component of the system controller 24. In such an embodiment, the X-ray controller 26 may be configured to provide power and timing signals to the X-ray source 12.

Moreover, the detector 22 is coupled to the system controller 24, which controls acquisition of the signals generated in the detector 22. In the depicted embodiment, the system controller 24 acquires the signals generated by the detector using a data acquisition system 28. The data acquisition system 28 receives data collected by readout electronics of the detector 22. The data acquisition system 28 may receive sampled analog signals from the detector 22 and convert the data to digital signals for subsequent processing by a processor 30 discussed below. Alternatively, in other embodiments the digital-to-analog conversion may be performed by circuitry provided on the detector 22 itself. The system controller 24 may also execute various signal processing and filtration functions with regard to the acquired image signals, such as for initial adjustment of dynamic ranges, interleaving of digital image data, and so forth.

In the embodiment illustrated in FIG. 1, system controller 24 is coupled to a rotational subsystem 32 and a linear positioning subsystem 34. The rotational subsystem 32 enables the X-ray source 12, collimator 14 and the detector 22 to be rotated one or multiple turns around the patient 18, such as rotated primarily in an x, y-plane about the patient.

It should be noted that the rotational subsystem 32 might include a gantry upon which the respective X-ray emission and detection components are disposed. Thus, in such an embodiment, the system controller 24 may be utilized to operate the gantry.

The linear positioning subsystem 34 may enable the patient 18, or more specifically a table supporting the patient, to be displaced within the bore of the CT system 10, such as in the z-direction relative to rotation of the gantry. Thus, the table may be linearly moved (in a continuous or step-wise fashion) within the gantry to generate images of particular areas of the patient 18. In the depicted embodiment, the system controller 24 controls the movement of the rotational subsystem 32 and/or the linear positioning subsystem 34 via a motor controller 36.

In general, system controller 24 commands operation of the imaging system 10 (such as via the operation of the source 12, detector 22, and positioning systems described above) to execute examination protocols (such as CCTA protocols) and to process acquired data. For example, the system controller 24, via the systems and controllers noted above, may rotate a gantry supporting the source 12, collimator 14, and detector 22 about a subject of interest so that X-ray attenuation data may be obtained at a variety of view angle positions relative to the subject. In the present context, system controller 24 may also include signal processing circuitry, associated memory circuitry for storing programs and routines executed by the computer (such as routines for executing image processing techniques described herein), as well as configuration parameters, image data, and so forth.

In the depicted embodiment, the image signals acquired and processed by the system controller 24 are provided to one or more processing components 30 (e.g., one or more general or special purpose microprocessors) for measurement data processing and/or reconstruction of images. In particular, the processing component (or components) 30 may execute one or more stored routines (such as routines stored in memory 38) to implement some or all of the data processing, data analysis, and image reconstruction and display steps disclosed herein, including those related to tuning coronary models and/or calculating blood flow parameters using projection or image data acquired using the imaging system 10. The processing component 30 may be one or more conventional microprocessors. The data collected by the data acquisition system 28 may be transmitted to the processing component 30 directly or after storage in a memory 38. Any type of memory suitable for storing data might be utilized by such an exemplary system 10. For example, the memory 38 may include one or more optical, magnetic, and/or solid state non-transitory memory storage structures. Moreover, the memory 38 may be located at the acquisition system site and/or may include remote storage devices for storing data, processing parameters (including model parameters and/or computational flow parameters), and/or processor-executable routines for image reconstruction, blood flow analysis, and/or fractional flow estimation, as described in greater detail below.

The processing component 30 may be configured to receive commands and scanning parameters from an operator via an operator workstation 40, typically equipped with a keyboard and/or other input devices. An operator may control the system 10 via the operator workstation 40. Thus, the operator may observe the reconstructed images and/or otherwise operate the system 10 using the operator workstation 40. For example, a display 42 coupled to the operator workstation 40 may be utilized to observe the reconstructed images and to control imaging. Additionally, the images may also be printed by a printer 44 which may be coupled to the operator workstation 40.

Further, the processing component 30 and operator workstation 40 may be coupled to other output devices, which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 40 may also be coupled to a picture archiving and communications system (PACS) 46. PACS 46 may in turn be coupled to a remote client 48, radiology department information system (RIS), hospital information system (HIS) or to an internal or external network, so that others at different locations may gain access to the raw or processed image data.

While the preceding discussion has treated the various exemplary components of the CT imaging system 10 separately, these various components may be provided within a common platform or in interconnected platforms. For example, the processing component 30, memory 38, and operator workstation 40 may be provided collectively as a general or special purpose computer or workstation configured to operate in accordance with the aspects of the present disclosure. In such embodiments, the general- or special-purpose computer may be provided as a separate component with respect to the data acquisition components of the system 10 or may be provided in a common platform with such components. Likewise, the system controller 24 may be provided as part of such a computer or workstation or as part of a separate system dedicated to image acquisition. In a present embodiment, the CT imaging system 10 may be a system suitable for coronary CT angiography (CCTA), a technique employed for imaging the coronary vasculature. An example of such a system is a Discovery CT750HD available from General Electric Company. Alternatively, an interventional X-ray system providing coronary X-ray angiography may provide the requisite information. An example of such a system is a Discovery IGS 730 available from General Electric Company.

Figure 2:
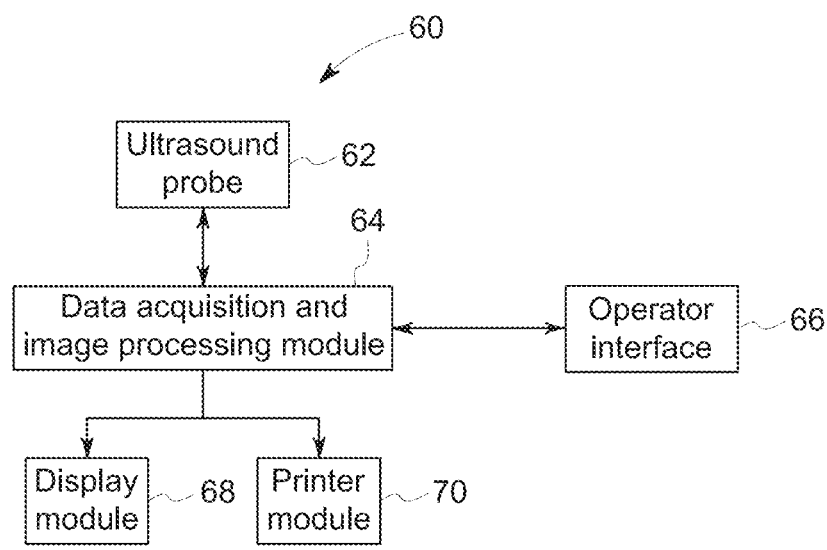
FIG. 2 is a block diagram depicting components of an ultrasound imaging system, in accordance with aspects of the present disclosure.

As noted above, in addition to anatomical image data derived using a CT system or interventional X-ray system (or other suitable anatomic imaging modality), certain implementations may also utilize ultrasound data. Turning to FIG. 2, an ultrasound system 60 suitable for use in accordance with the present disclosure is depicted.

As depicted, the ultrasound imaging system 60 includes an ultrasound probe 62, a data acquisition and image-processing module 64, an operator interface 66, a display module 68 and a printer module 70. The ultrasound imaging system 60 uses the ultrasound probe 62 for transmitting a plurality of ultrasound signals into an object, such as into the cardiac or thoracic region of a patient being imaged, and for receiving a plurality of reflected ultrasound signals therefrom. The ultrasound probe 62 may include an array of transducer elements for transducing mechanical or electrical energy to acoustic energy, and vice versa, to facilitate this process. In certain embodiments, the ultrasound probe 62 can be hand-held or mechanically positioned such as by using a robotic assembly, or otherwise placed in position. The ultrasound system 60 may employ 2D (so called two-dimensional) beam-formation technology with mechanically swept beams or 2D phase-array technology to obtain the desired volumetric ultrasound data, as discussed herein.

The data acquisition and image-processing module 64 sends signals to and receives information from the ultrasound probe 62. Thus, the data acquisition and image-processing module 64 controls strength, width, duration, and a frequency of the plurality of ultrasound signals transmitted by the ultrasound probe 62, and receives the information contained in the plurality of reflected ultrasound signals from the object to a plurality of discernible electrical and electronic signals. Once the information is obtained, an ultrasound image of the features or characteristics of interest within the imaged volume is reconstructed/presented in accordance with generally known reconstruction/presentation techniques. In addition, other forms of information, such as blood flow, can be derived from ultrasound data.

The operator interface 66 may include a keyboard, a mouse, and other user interaction devices. The operator interface 66 can be used to customize a plurality of settings for an ultrasound examination, and for effecting system level configuration changes. The operator interface 66 is connected to the data acquisition and image-processing module 64 and may be used to command the data acquisition and image-processing module 64 to display information on the display module 68 or to print information on the printer module 70. For example, the display module 68 may receive information from the data acquisition and image-processing module 64 and presents the image of the region of interest imaged by the ultrasound probe 62. The printer module 70 may be used to produce a hard copy of the ultrasound image in either gray-scale or color.

In a present embodiment, the ultrasound system 60 is capable of acquiring one or more types of volumetric flow information within a vessel. That is, the plurality of reflected ultrasound signals received by the ultrasound probe 62 are processed to derive a spatial representation that describes one or more flow characteristics of blood within the imaged vasculature. For example, in one embodiment, the ultrasound system 60 is suitable for deriving spectral or color-flow type Doppler information pertaining to one or more aspects of blood flow or velocity within the region undergoing imaging (e.g., spectral or color flow Doppler velocity information for planar or volume flow estimation). Similarly, various volumetric flow algorithms may be used to process or integrate acquired ultrasound data to generate volumetric flow information corresponding to the sample space inside a blood vessel.

With the foregoing systems in mind, one or both of CCTA and ultrasound data may be acquired in accordance with certain aspects of the described implementations.

(1) Contrast Dynamics—With respect to a first set of approaches to be discussed, the flow dynamics of a contrast agent imaged using a CT or CCTA imaging system are determined and used to estimate coronary flow and/or fractional flow reserve.

(A) Using the spatial contrast agent concentrations obtained at one or more cardiac phases (i.e., snapshots) to tune a coronary circulation model—In one implementation that uses contrast dynamics to estimate coronary flow, which may include fractional flow reserve, the spatial concentration of a contrast agent is obtained at one or more cardiac phases (e.g., "snapshots"). The spatial concentration of the contrast agent is then used to tune a coronary circulation model to be patient specific. Even though the discussion is provided in the context of coronary circulation both to provide a useful example and to facilitate explanation, it should be noted that this approach is not limited to such applications and may also be suitable for tuning blood flow models of other organs in the human body such as brain, liver, kidney, and so forth.

With respect to this approach, there is a spatial gradient in average contrast opacification in CTA images from a proximal to a distal coronary artery segment in the presence of a stenosis, i.e., a narrowing of the coronary vessel. The present approach assumes that the higher opacification gradients observed in the presence of a stenosis is due to low flow. This is plausible as a functionally significant stenosis in a coronary artery segment will lead to low blood flow in that region under rest/hyperemic conditions. Studies conducted in support of the present approach modeled contrast agent propagation in realistic stenosis models and showed that there is a higher drop in average contrast concentration over the length of the computational domain at lower flow rates. Results of these studies are shown in FIG. 3, which depicts average contrast agent concentration (y-axis) along the length (x-axis) of a realistic coronary artery stenosis model at two different flow rates, 500 ml/min and 200 ml/min.

Figure 3:
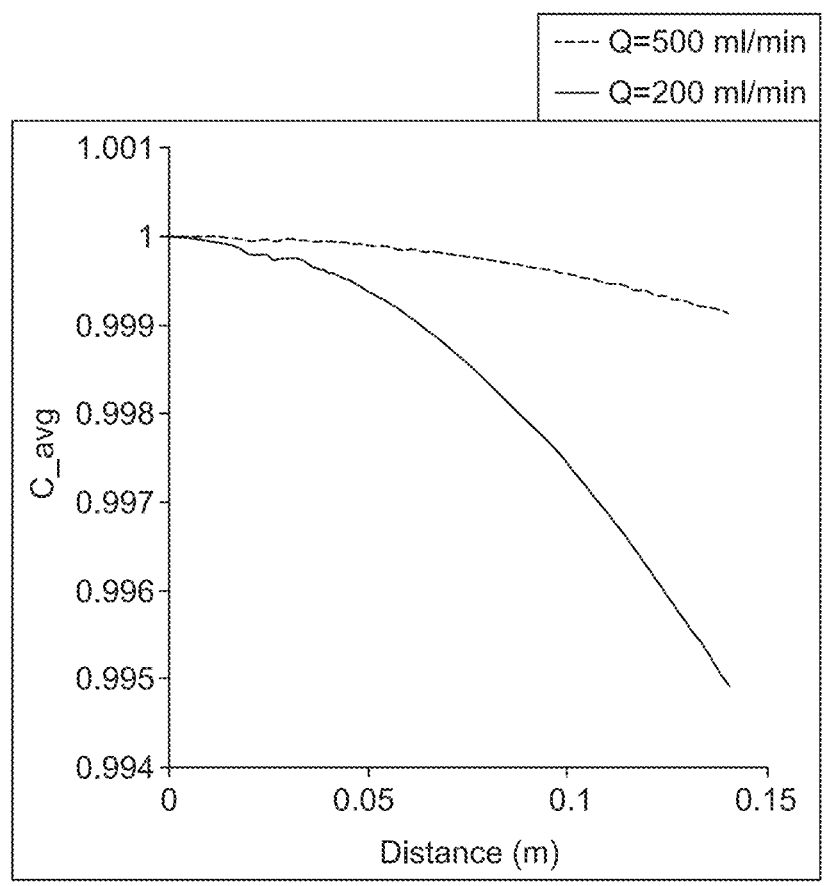
FIG. 3 is a graph depicting average contrast agent concentration along the length of a coronary artery stenosis model at two flow rates, in accordance with aspects of the present disclosure.

As shown in FIG. 3, the drop in concentration over a given distance is related to flow rate. Assuming this phenomenon is not limited to stenosed vessels, two healthy vessels with different flow rates are also likely to have different contrast concentration (i.e, opacity) drops for different flow rates over the same distance. Such a drop in concentration can be used to tune a blood flow model and estimate flow rates in the imaged vessels.

By way of example, a more detailed explanation in the context of coronary arteries is provided. In this example, a 1D model of the coronary circulation is employed. Note that a 1D model is employed simply to facilitate explanation and the approach is applicable to 3D blood flow models as well. In this 1D model the large vessels (e.g., ascending aorta, coronary epicardial vessels) are modeled as axi-symmetric vessel segments with the blood flow dynamics in those vessels governed by the following equations:

$$\frac{\partial A}{\partial t} + \frac{\partial Q}{\partial z} = 0 \qquad (1)$$

$$\frac{\partial Q}{\partial t} + \alpha \frac{\partial}{\partial z}\left(\frac{Q^2}{A}\right) + \frac{A}{\rho}\frac{\partial p}{\partial z} - 2\pi\frac{\mu}{\rho}s'\frac{Q}{A} = 0 \qquad (2)$$

$$p - p_0 = \beta\frac{\sqrt{A} - \sqrt{A_0}}{A_0}. \qquad (3)$$

Figure 4:
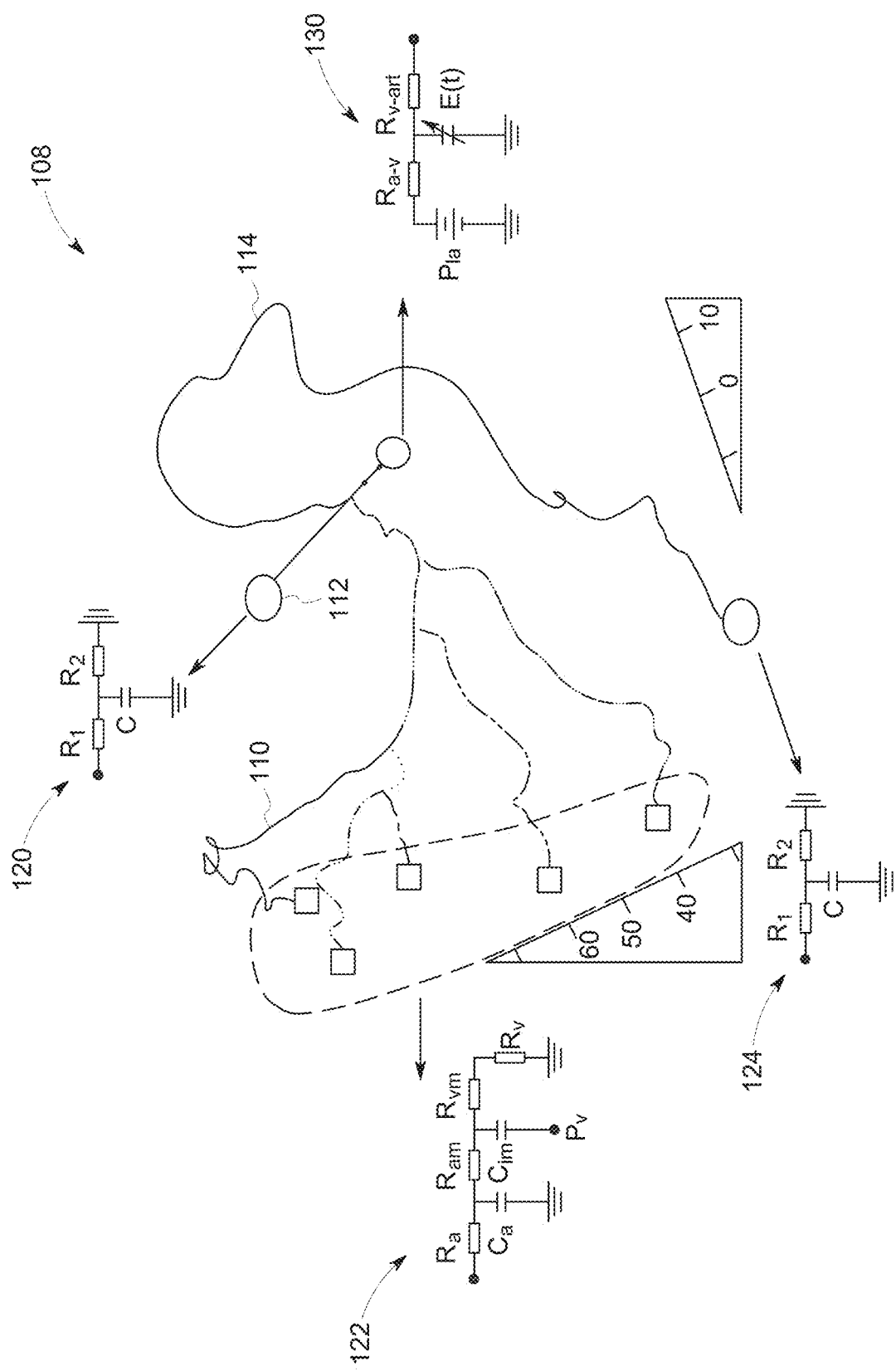
FIG. 4 schematically depicts a 1D (so called one-dimensional) coronary circulation model having lumped or 0D (so called zero-dimensional) models used as inflow or outflow boundary conditions, in accordance with aspects of the present disclosure.

Here, $\mu$ is the dynamic viscosity and $\rho$ is the density of blood, $A(z,t)$ is the vessel cross-sectional area and $Q(z,t)$ is the volumetric flow rate. s is a radial profile function relating the velocity profile in the z direction to Q and A, $$u_z = \frac{Q}{A}s\left(\frac{r}{R}\right)$$

and $\alpha = \int_0^1 2s(u)^2 u\, du$. p is the blood pressure, $A_0$ is the cross-sectional area when $p=p_0$ and $\beta$ is a parameter related to vessel stiffness. Boundary conditions needed to solve equations (1-3) are provided in the form of zero-dimensional (0D) or lumped parameter models. An example of certain such 0D or lumped models used as inflow and outflow boundary conditions in a 1D coronary circulation model is shown in FIG. 4, which also illustrates corresponding lumped models for the heart, systemic circulation, and coronary microcirculation. In particular, with respect to the coronary vasculature, a left coronary tree 110, ascending aorta 112, and right coronary tree 114 are depicted as part of the coronary circulation model 108. Outflow boundary conditions are modeled, in this example, by a systemic circulation lumped model 120, a left coronary microcirculation lumped model 122, and a right coronary microcirculation lumped model 124. In this example, an inflow boundary condition is modeled by a heart lumped model 130.

As described above, the parameters in the lumped model(s) need to be personalized (such as based upon patient specific observation, image analysis, and/or physiological monitoring) in order to generate a patient-specific model. In one implementation, these parameters are tuned to obtain the same drop in contrast concentration in each coronary vessel segment as that measured from the CTA images. In doing so, a flow rate is obtained for each vessel segment that matches measured concentration drops. The flow rate in the terminal vessel segments can be summed up to give the total coronary flow.

In one implementation, the 1D model uses, in addition to vessel centerline and cross-sectional sectional area, the average contrast concentration along the centerline at one or more cardiac phases. While concentration cannot be directly obtained from CTA images, it does provide information on X-ray attenuation (i.e., opacity) due to the presence of contrast, in terms of Hounsfield units (HU). Since the pixel intensity value, as characterized in HU, may be generalized as being proportional to the contrast concentration, the intensity or opacity as characterized in HU may be used as a surrogate for contrast concentration. Using dual-energy CT principles, one can decompose the linear attenuation values within the patient into two density distributions of known materials (such as water and iodine). In this case, one can determine the contrast concentration directly.

Thus, in one implementation the average contrast concentration along the centerline can be obtained as the average HU value at each cross-sectional area along the centerline. Ideally, the average HU value would be obtained along the coronary tree at a single instance or cardiac phase. However, in practice there will typically be some degree of propagation of the contrast during the duration of the scan and the measured average HU value at each cross-sectional area will be some average over the scan duration. The propagation of contrast agent in the 1D model is modeled using the following equation:

$$\frac{\partial \bar{c}}{\partial t} + \frac{Q}{A}\frac{\partial \bar{c}}{\partial z} = D_{\mathit{eff}} \frac{\partial^2 \bar{c}}{\partial z^2} \qquad (4)$$

Here Q(z,t) is the volumetric flow rate, A(z,t) is the vessel cross-sectional area, $\bar{c}$(z,t) is the contrast agent concentration averaged over the vessel cross-sectional area and $D_{\mathit{eff}}$ is an effective diffusion coefficient.

To solve equation (4), a boundary condition is needed for the average concentration at the inflow boundary (where the heart lumped model 130 is applied) as a function of time. This could, for example, be obtained using an image analysis feature that uses low dose scans (e.g., scout or localizer scans) to monitor the contrast attenuation in a region of interest before initiation of the actual scan. When the contrast attenuation reaches a certain threshold (e.g., a threshold prescribed by the technician), the scan is initiated. Thus, one could use such an analysis of low dose image data to obtain inflow boundary conditions for the above convection-diffusion equation (4). Equation (4), along with 1D pulse propagation equations, can then be solved, starting with assumed lumped model parameters for the coronary microcirculation. The predicted HU distribution is then compared against the measured HU distribution along the coronary tree. As noted previously, the measured HU values are actually an average over the scan duration. So, the predicted distributions may also be averaged over the scan duration and it is this average that is compared against the measured values. Depending on the difference, the lumped model parameters are adjusted. The equations are solved once again with the adjusted parameters until the predicted and measured HU distributions match within a specified tolerance.

Figure 5:
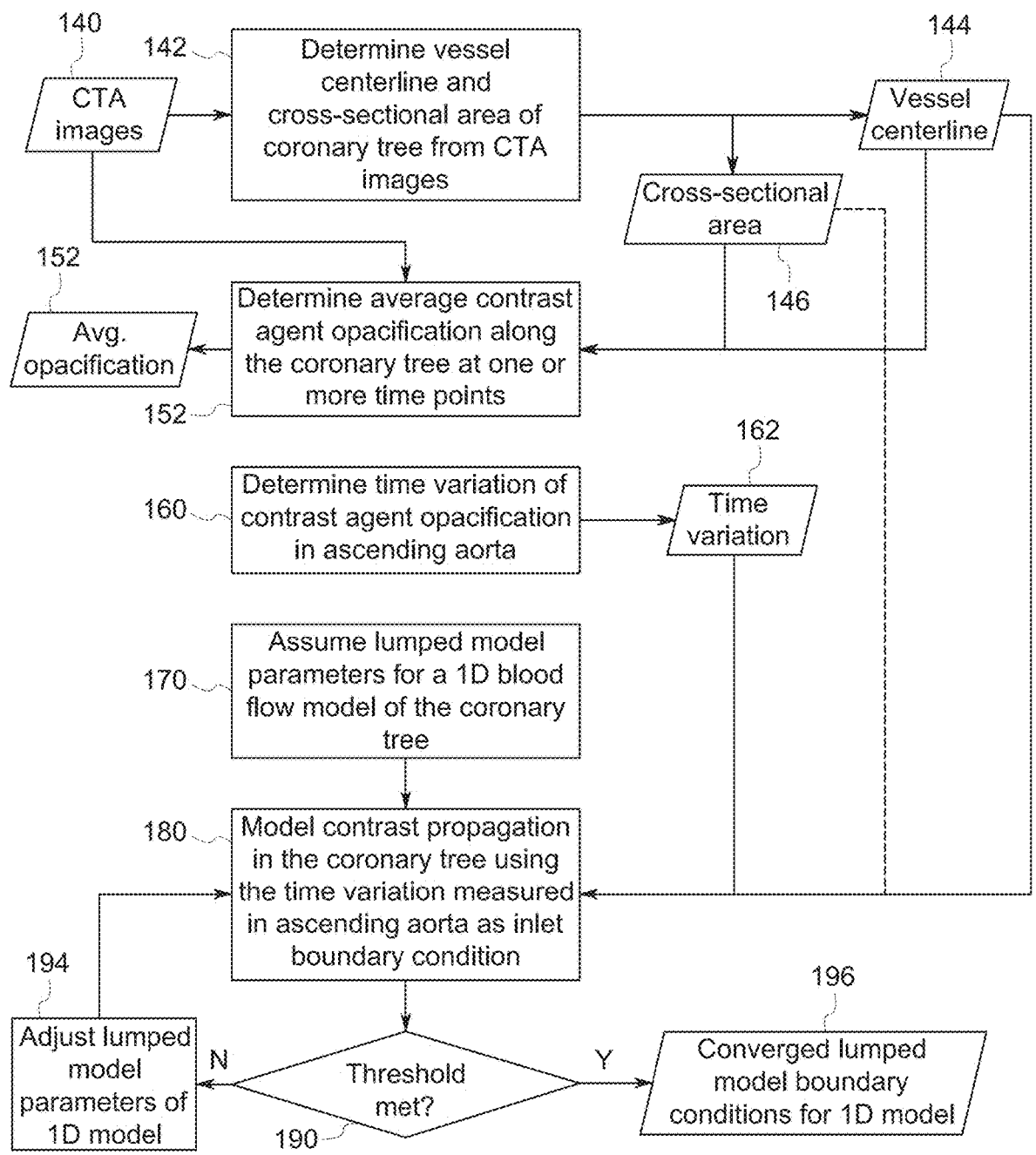
FIG. 5 depicts a process flow for tuning a coronary model, in accordance with aspects of the present disclosure.

This approach is outlined in the flowchart shown in FIG. 5. In this example, CTA images 140 are acquired either in a current or previous examination, and analyzed to determine (block 142) vessel centerline(s) 144 and cross-sectional area 146 of the coronary tree. These parameters may be used in conjunction with the CTA images 140 to determine (block 150) the average cross-sectional contrast agent opacification 152 along the coronary tree at one or more time points. The time variation 162 of contrast agent opacification 152 in the ascending aorta (or other relevant vasculature) is determined (block 160) through a low dose scan performed separate from (e.g., before the initiation of) the actual scan. One or more model parameters for a 1D blood flow model of the coronary tree are initially assumed (block 170). The contrast propagation in the coronary tree is modeled (block 180) using the vessel centerline(s) 144 and cross-sectional area 146 previously determined and the time variation 162 observed in the ascending aorta (or other relevant vasculature) as an inlet boundary condition. A determination is then made (decision 190) whether the predicted contrast opacification averaged over scan duration minus the measured average opacification 152 at one or more time points (i.e., the predicted values minus the observed values) is within a specified tolerance or threshold. If not, the model parameters of the 1D model are adjusted (block 194) and the modeling process (block 180) is repeated. If yes, however, the converged model boundary conditions (block 196) for the 1D model are accepted and output for analysis in the context of coronary flow and/or fractional flow reserve, as discussed herein.

In certain implementations, geometrical features, such as vessel curvature, may be accounted for in the 1D model. As will be appreciated, curvature can affect the flow in various ways. For example, as the flow navigates the curvature, the velocity profiles get skewed due to centrifugal forces. This could lead to higher wall shear stresses and result in an additional pressure drop. Curvature can also lead to the formation of secondary vortices, which can be effective at mixing contrast agents. Therefore, in certain implementations, the effect of curvature (or other geometrical features) on both pressure drop and contrast mixing may be parameterized to address these effects. The parametric model may then be incorporated into the 1D equations.

It may also be appreciated that certain of the preceding discussion, such as that pertaining to FIG. 3, relate to a steady flow context. However, in practice, flow through the large vessels, including the coronary arteries, may be unsteady. Thus, contrast concentration at any location along the coronary tree at an instant in time is going to depend on the flow rate profile shape. In the 1D model, in addition to the heart and coronary microcirculation lumped model parameters, vessel stiffness also plays a role in determining the flow rate profile shape. If vessel cross-sectional area 146 in the coronary arteries can be determined at multiple cardiac phases, that information can be used to tune vessel stiffness by minimizing the error between predicted and measured cross-sectional areas 146. Alternately, the vessel cross-sectional area in the ascending aorta may be determined at multiple cardiac phases and the vessel elasticity can be assumed to be function of radius in the aorta and the coronaries as given by:

$$\frac{Eh}{r_0} = k_1 \exp(k_2 r_0) + k_3 \qquad (5)$$

where E is the modulus of elasticity, h is the vessel wall thickness, $r_0$ could be the radius at diastole and $k_1$, $k_2$, and $k_3$ are constants. These constants, in one example, can be determined by minimizing the error between predicted and measured cross-sectional areas 146 in the ascending aorta 112. The heart lumped model 130 can be tuned using left ventricular blood volume measured from CTA images 140 as described in the section on cardiac dynamics. This leaves only the coronary microcirculation lumped parameters to be determined, minimizing the number of unknowns.

The described approach is not limited to CT angiography and can be used with other imaging techniques where a contrast agent is used to visualize the blood vessels in the human body. An example of one other suitable technique is X-ray angiography. In X-ray angiography, a contrast agent is injected directly into an artery through interventional means and 2D images are acquired at a rate of about 15-30 images per second as the contrast agent propagates through the blood vessel tree. Spatial as well as temporal contrast opacification distribution along the tree is thus available from X-ray angiograms. The vessel centerline and cross-sectional area (block 142 and 144 in FIG. 5) in this case could be obtained from bi-plane imaging, where simultaneous images from two offset (e.g., orthogonal) planes are acquired, or from a rotational scan using the C-arm. Since temporal images are available, the boundary condition needed for concentration at the inflow boundary (block 162 in FIG. 5) can be obtained by fitting a curve through the opacification time history at the injection site. The parameters of the 1D model can then be tuned as before so that the predicted and measured spatial contrast concentration distributions match within a specified tolerance.

It may be noted that the present approach differs from previous approaches in certain significant aspects. For example, certain previous approaches estimate flow rate using a patient-specific transluminal attenuation gradient (TAG) obtained from CTA images. The present approach differs from such approaches in certain ways. For example, TAG in the previous approach is defined as the difference in contrast concentration between two locations along the coronary tree obtained at the same instance in time divided by the distance between those two locations. However, in the present approach, as described above, TAG is not computed. In addition, the present approach does not assume that the HU values along the coronary tree are obtained at the same instance, which neglects contrast propagation over the scan duration. Instead, the present approach takes into account that what is in fact measured is the HU value averaged over the scan duration and during the optimization step in the present approach the predicted HU distributions are averaged over the scan duration and only then compared against the measured values.

In addition, in the present approach flow rate is determined by tuning the coronary microcirculation model to minimize the difference between predicted and measured contrast concentration distributions, which differs from prior approaches. In addition, prior approaches assume that the flow rate is constant between the TAG locations, whereas no such assumptions is employed in the present approach. In general, while the time average flow rate between the two locations are the same, the instantaneous flow rates can be different.

Lastly, prior approaches typically assume that the contrast concentration at the coronary ostium is propagated along the coronary tree without any diffusion. No such assumptions are made in the present approach. Instead, both convection and diffusion of the contrast agent is allowed.

(B) Injecting a pattern contrast bolus, taking one or more snapshots, and estimating location dependent velocity—In a further implementation that uses contrast dynamics to estimate coronary flow and/or fractional flow reserve, a "patterned" contrast bolus is administered (e.g., injected) to facilitate identification of the contrast flow (and thereby flow rate) at one or more positions in the coronary tree (or any other suitable blood vessels).

Figure 6:
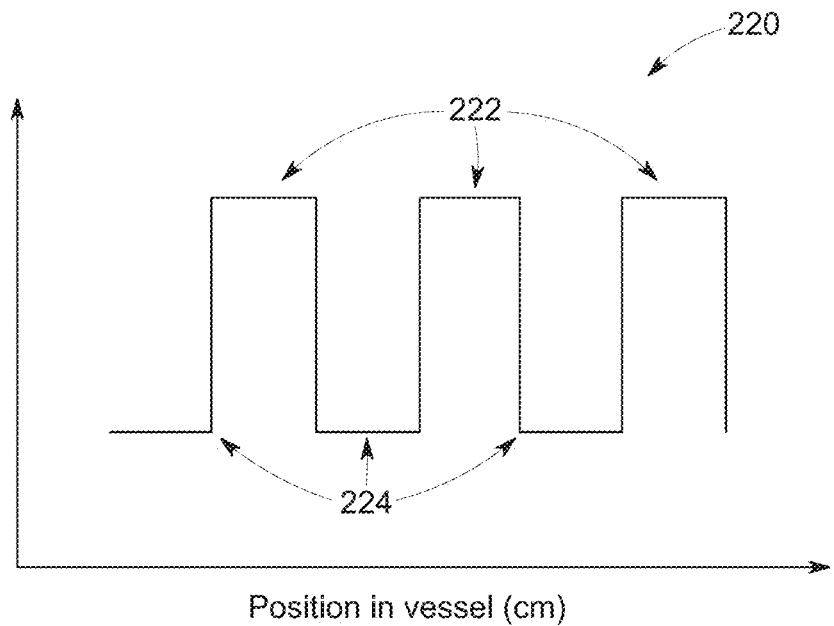
FIG. 6 depicts an idealized patterned bolus of contrast agent in terms of contrast agent concentration and blood vessel position, in accordance with aspects of the present disclosure.

As used herein a patterned bolus is defined as a contrast injection that has intentional fluctuations in the concentration of contrast administration. A traditional contrast injection consists of a single pulse, where the total injection time can vary and the flow rate is not necessarily constant. A patterned bolus, instead, has more than one peak flow rate (i.e., more than one pulse) separated by intervals of non-peak flow rate and follows a pattern such as a pulse train or a sinusoidal pattern. The contrast injection can also be alternated with saline injection to keep the overall flow rate more constant, with the contrast concentration varying between high and low pulses. This can be achieved by an injector with a contrast agent reservoir and a saline reservoir, which are alternatingly accessed or in different proportions. An example of a patterned bolus 220 (as a function of location) is shown in FIG. 6. In this example, the pattern is shown as it appears at the injection site, with alternating intervals of contrast administration 222 (contrast concentration or quantity is shown on the y-axis) and saline administration 224. As shown, over time, each "pulse" of contrast moves or is translated downstream (x-axis) relative to blood flow. A single pattern would be seen when plotted for one fixed location as a function of time.

Figure 7:
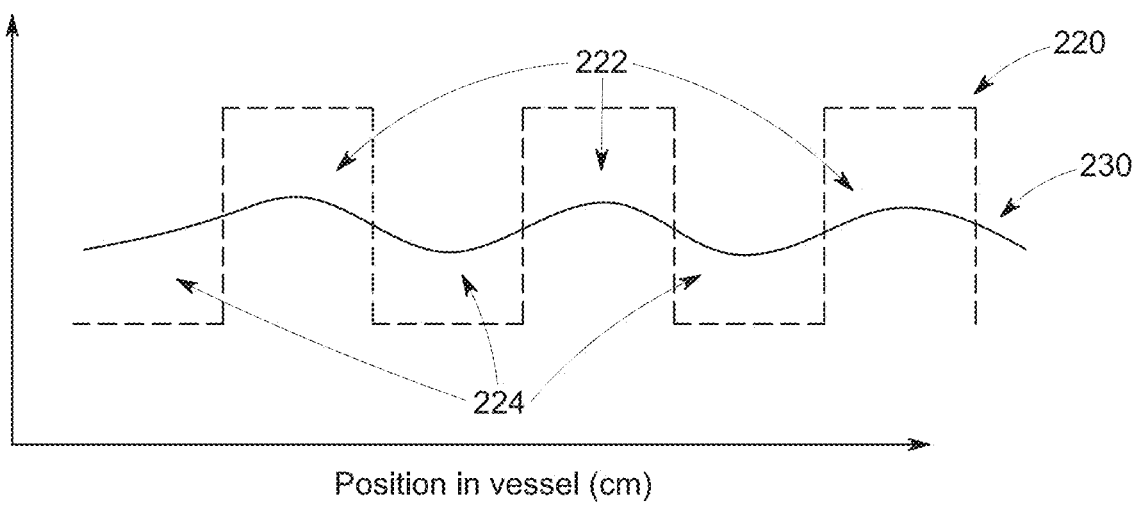
FIG. 7 depicts the patterned bolus of FIG. 6 downstream from an administration site, in accordance with aspects of the present disclosure.

As will be appreciated, the bolus pattern 220 will gradually fade as the blood flows through the vessels. While the bolus pattern 220 looks very crisp (i.e., has sharp or defined edges, as shown in FIG. 6) near the injection site, the pattern 230 inside the coronary tree may be less distinct, as shown in FIG. 7, though still possessing highs 222 and lows 224 of contrast concentration. As may be appreciated, the pattern 230 may be stretched out (e.g., spatially) and the modulation amplitude may be partly lost or difficult to discern.

Figure 8:
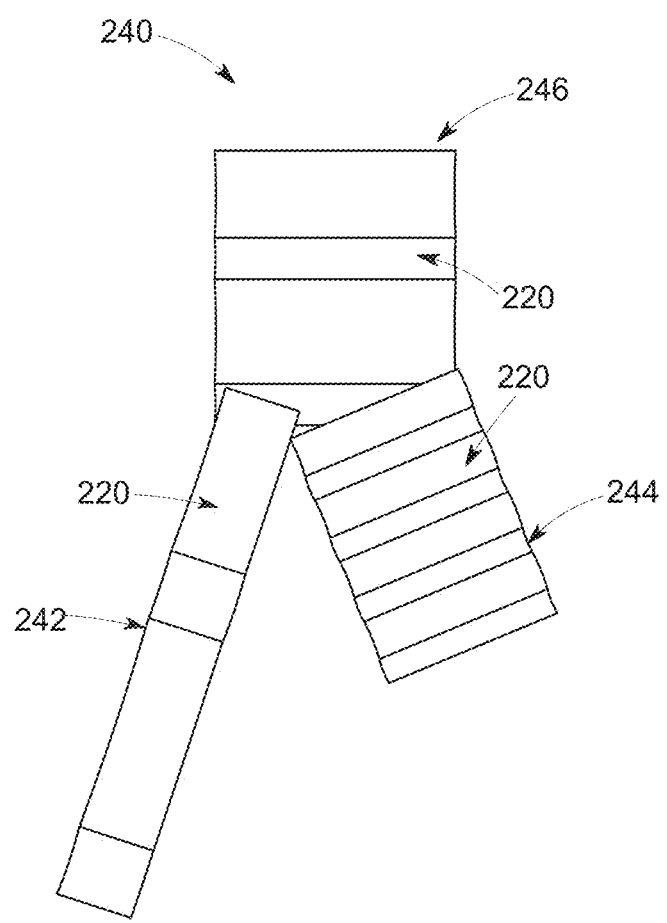
FIG. 8 schematically illustrates the interplay between vessel size and band spacing in a patterned bolus context, in accordance with aspects of the present disclosure.

By analyzing the spatial distribution of the bolus pattern (such as over time), properties of the blood flow may be derived, such as blood velocity or flow, as generally illustrated in FIG. 8 which depicts a branched vessel 240 having a narrower branch 242, a wider branch 244, and a root 246 and through which a pulsed contrast bolus 220 is passing. As simplistically illustrated in FIG. 8, an expanded pattern 220 (such as is present in the narrow branch 242) is indicative of higher coronary flow rate (i.e., high speed) while a compressed pattern 220 (such as is present in the wider branch 244) is indicative of slower coronary flow rate (i.e., slow speed).

The combination of the contrast injection parameters, such as shown in FIG. 6, and the spatio-temporal contrast agent distribution, such as shown in FIG. 8, can also be used to tune the parameters of the 1D coronary model, as discussed in the preceding example. The 1D coronary model in turn can then be used to assess whether or not a lesion is flow-limiting.

Another optimization possibility is to change the contrast injection protocol. Currently, a large volume of contrast is continuously injected in order for the entire vesicular structures to be filled with iodine. Since the "dynamics" of the flow is of interest in the present example instead of the "steady state", the injection may be changed to a series of "short bursts" of contrast. This will provide multiple "wave fronts" to allow us to use the temporal information. That is, both the rising edge as well as the trailing edge of the contrast can be observed. By monitoring the timing delay between successive contrast arrivals, various parameters and boundary conditions can be estimated, since how and when different bursts of contrasts are injected is known.

(C) Projection Based Bolus Tracking—In a further contrast dynamics approach to estimating coronary flow and/or fractional flow reserve, a bolus of contrast agent may be administered (e.g., injected) to a patient and projection data of the heart and coronary vessels generated. Projection data generated as part of the imaging process may be monitored as the bolus in the chambers of the heart clears. As such, for a period of time, the coronaries will be opacified, while the heart chambers begin to clear of contrast agent. During this transitional period of time, the coronary vessels may be visible in the projection data (e.g. in a full heart coverage scan) and can be used to estimate contrast dynamics. While the coronary arteries are opacified, the CT gantry may be continually rotated or parked at angular location where the coronary vessels would be most visible in projection data. In one embodiment, the projection data only are used to estimate cross-sectional area of vessels. In an alternate embodiment, if the CT gantry is rotated, a 3D representation of the heart volume can be generated and cross-sectional areas of the coronary arteries estimated, so that the contrast dynamics in the projection data may be used, along with knowledge of the cross-sectional area of the vessels, to estimate flow rate in the coronary arteries. With this in mind, FIGS. 9 and 10 depict flow charts explaining aspects of such an implementation, with FIG. 9 describing steps in a data acquisition and FIG. 10 describing steps in processing the data in such an implementation.

Figure 9:
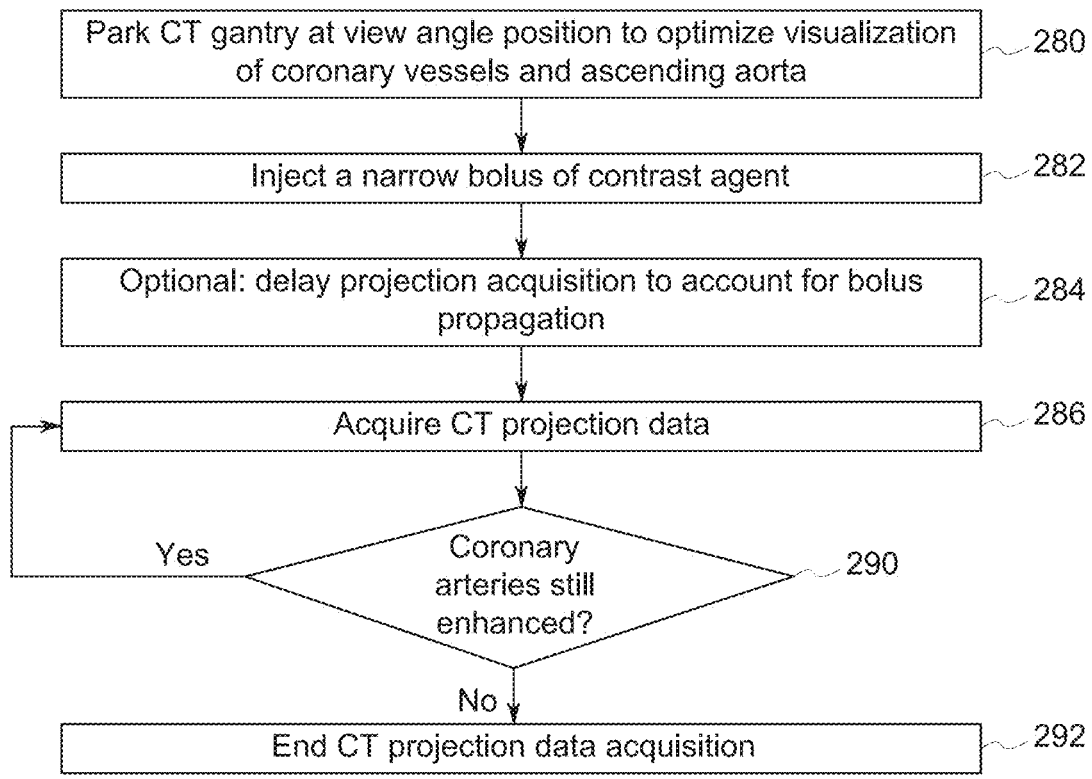
FIG. 9 depicts a process flow for CT projection data acquisition, in accordance with aspects of the present disclosure.

Turning to FIG. 9, in this example, the X-ray source 12 is positioned (block 280) at a view angle selected so as to optimize visualization of coronary vessels and the ascending aorta, such as by parking a CT gantry so as to position the source 12 at a suitable view angle. With the source 12 so positioned, a "narrow" (e.g., tightly defined and brief in duration) bolus of contrast agent is administered (block 282) to the subject. An option delay (block 284) may be provided to account for the time it takes for the contrast to propagate from the administration site to the region of interest. Once the narrow bolus is present in the region of interest (e.g., the heart chambers and coronary vasculature) CT projection data is acquired (block 286) over a specified time interval.

A determination is made (decision block 290) based on the acquired projection data as to whether the coronary arteries are still enhanced, i.e., opacified, above a specified threshold. If the coronary vasculature is still enhanced beyond the threshold, CT projection data continues to be acquired over an additional time interval. If not, projection data acquisition is ended (block 292).

Figure 10:
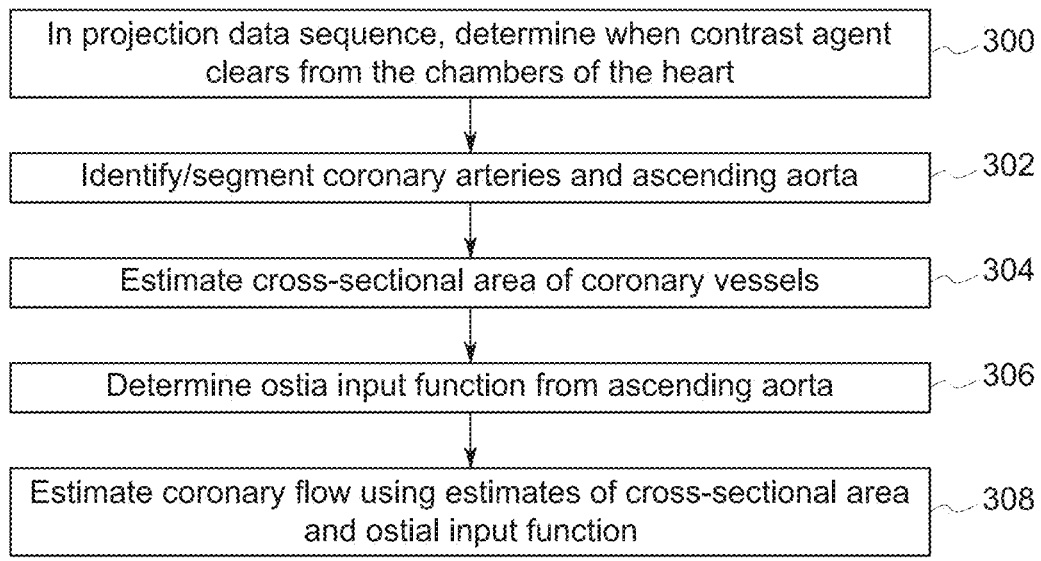
FIG. 10 depicts a process flow for CT projection data processing, in accordance with aspects of the present disclosure.

Once the acquisition process of FIG. 9 is complete, processing of the projection data may be performed, as outlined in FIG. 10. In this example, the sequentially acquired projection data is analyzed (block 300) to determine when the contrast agent clears from the heart chambers, such as by comparison of opacity versus a threshold value corresponding to contrast clearance. Coronary vessels (e.g., arteries) and/or the ascending aorta are identified (block 302), and in some implementations segmented, within the projection data. Cross-sectional areas of the identified coronary vessels are estimated (block 304). In the depicted example, ostia input function (i.e. opacified or non-opacified blood as represented with HU values) from the ascending aorta is then determined (block 306). The estimated cross-sectional vessel areas and ostial input function are then used to estimate coronary flow (block 308).

(D) Bolus Tracking Across Cardiac Cycles—In addition to the various intra-cycle 4D (i.e., 3D spatial plus temporal) techniques discussed herein (i.e., where cardiac multi-phase image information, such as between 5% to 95% of the interval between adjacent R peaks in the patient's EKG waveform during the cardiac cycle, is acquired within one heart cycle), other implementations may employ 4D techniques across heart cycles, i.e., acquired over more than one cardiac cycle. For example, such a 4D technique may involve imaging at 75%, "175%", "275%", etc. of a typical interval between R peaks, i.e. over more than one cardiac cycle.

By way of example, if two or three frames, i.e. cardiac cycles, at the same cardiac phase location are acquired from consecutive beats, the difference in image enhancement may provide a degree of "flow" information. To address frame-to-frame repeatability (i.e., spatial registration), a non-rigid registration may be applied to align frames. To generalize, data could be acquired for 2 or more frames at various user defined intervals (e.g., over consecutive beats, at every second beat, every third beat, and so forth). Further, the X-ray dose could differ between frames. For example, in a three-frame implementation, the middle frame could be full technique X-ray dose for the diagnostic CCTA volume. However, earlier and/or later frames could be acquired at lower dose.

Figure 11:
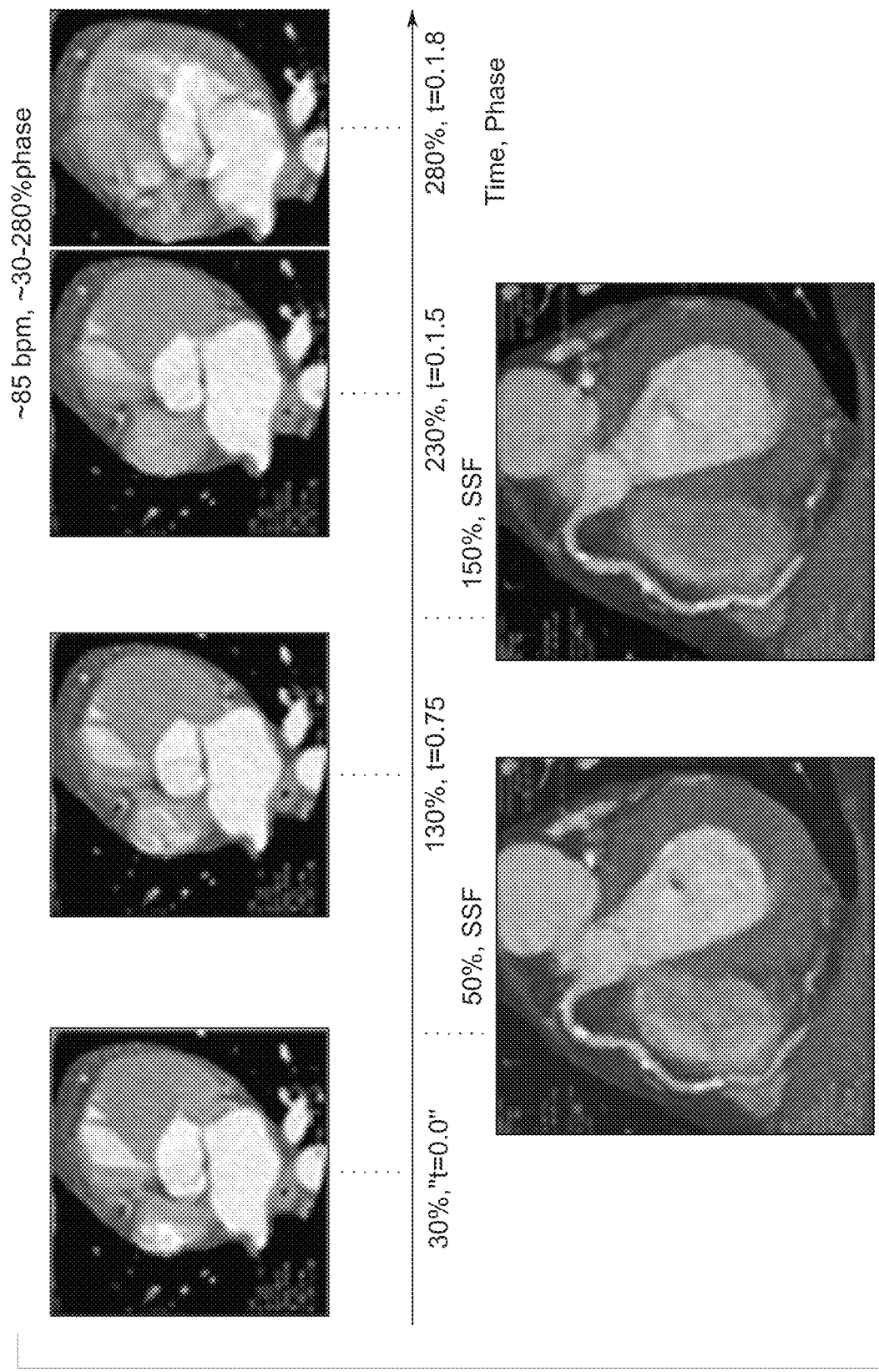
FIG. 11 depicts contrast effects and timing over multiple heart beats, in accordance with aspects of the present disclosure.

With the preceding in mind, FIG. 11 depicts image frames from a clinical example exam where data was acquired at more than one time point across multiple cardiac cycles. In particular, the depicted example illustrates contrast timing over 2.5 heart beats, at approximately 85 beats per minute and approximately 30%-280% of the R peak interval. As shown, there is less contrast in the right chamber at 150% of the R peak interval (i.e., the middle point of the second beat) than there is at 50% of the R peak interval (i.e., the middle of the first beat).

(E) Stress and Rest Acquisition for Estimating Physiological Parameters (e.g., coronary flow reserve)—In a further contrast dynamics approach, imaging at both a stress (i.e., vasodilation) and a rest interval may be used to derive coronary flow and/or fractional flow reserve estimates. By way of example, such acquisitions may be performed in the context of cardiac perfusion CT imaging, the protocols of which typically include multiple acquisitions and multiple administrations of contrast. In such examinations, the added dose/contrast burden is justified due to the added clinical value provided by these scans.

In a present approach, two scans (e.g., a stress (i.e., vasodilation) scan and a resting scan) could also be used to enable computation of physiological parameters, such as coronary flow reserve. Coronary flow reserve (CFR) measures the ratio between the normal flow and the maximum flow that can be measured under dilation of the microvasculature. This vasodilation can be pharmacologically induced using adenosine. The techniques described in certain of the preceding examples could be used to measure the coronary flow for the resting and stress scans and the comparison of flow between the scans would give an estimate of CFR. Having both CFR and fractional flow reserve (FFR) together may be more valuable than an FFR measurement alone in guiding treatment decisions.

Further, the data collected in the stress and resting scans could also be incorporated in the CFD model to provide a more accurate assessment of flow rates and pressures under varying conditions, which may provide more accuracy and precision. Finally, based on a comparison of the cross-sectional area of the lumen view at various places on a coronary artery, information about the elasticity/dilatability of each section of the coronary tree may be inferred, which can help improve the model further and provide useful information regarding plaque characteristics.

(2) Cardiac Dynamics—With respect to a second set of approaches to be discussed, the position and/or motion dynamics of the imaged heart and associated cardiac vasculature are determined and used to estimate cardiac output. The estimated cardiac output is then used to tune the parameters of a heart lumped model 130 used as inflow boundary condition in a coronary circulation model. This model is then used to predict coronary flow and/or fractional flow reserve.

Figure 12:
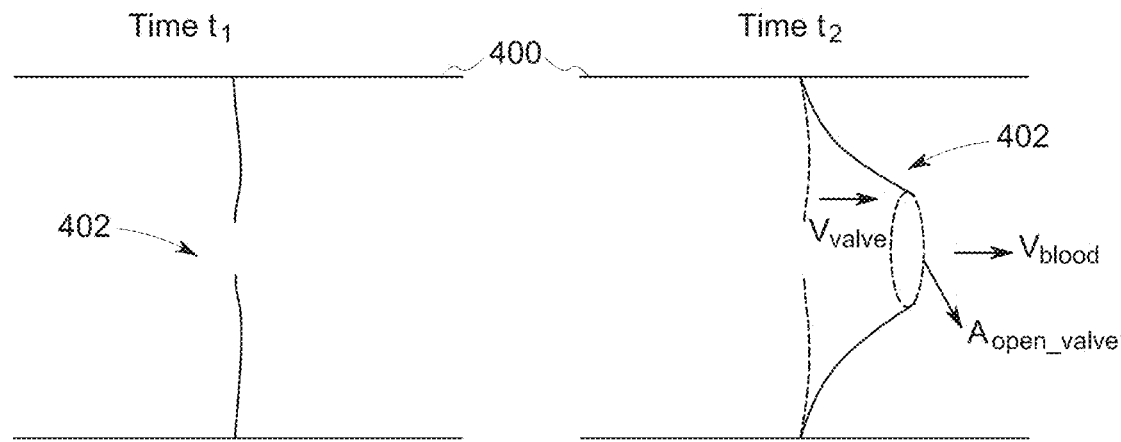
FIG. 12 depicts a closed and open valve in the context of a vessel, in accordance with aspects of the present disclosure.

(A) Determine the speed at which the aortic valve opens/closes to estimate maximum blood velocity and peak cardiac output—In a first cardiac-dynamics-based approach to estimating coronary flow and/or fractional flow reserve, the position of the valve is analyzed at different points in time in image data and the position data is used to estimate the maximal velocity of the valve. Concepts relevant to the present discussion are illustrated in FIG. 12, which shows a vessel 400 having a valve 402 in a closed position, position$_1$, (leftmost figure) corresponding to a first time, $t_1$, and open position, position$_2$, (rightmost figure) corresponding to a second time, $t_2$. Concepts related to valve velocity, $v_{valve}$, blood velocity, $v_{blood}$, and the cross-sectional area associated with the open valve, $A_{open\ valve}$ are illustrated with respect to the figures.

In accordance with this approach, the maximal valve velocity may be estimated by:

$$v_{Valve}^{Max} = (\text{position}_2 - \text{position}_1)/(t_2 - t_1) \quad (6)$$

From this, the peak blood velocity may be estimated by:

$$v_{Blood}^{Max} = c_1 \cdot v_{Valve}^{Max}. \quad (7)$$

The peak blood velocity may in turn be used to estimate the peak blood flow:

$$\text{flow}_{Blood}^{Max} = c_2 \cdot A_{open\ valve} \cdot v_{Blood}^{Max} \quad (8)$$

where $c_1$ and $c_2$ are empirical scale factors or correction factors.

Thus, in this manner, images of the open and closed valve at known times can be analyzed to determine the respective positions of all or part of the valve 402 at the known times, from which a valve velocity may be calculated. The valve velocity (e.g., a maximal velocity) may in turn be used to determine the blood velocity which can be used in conjunction with the area of the valve to estimate a measure of blood flow.

Figure 13:
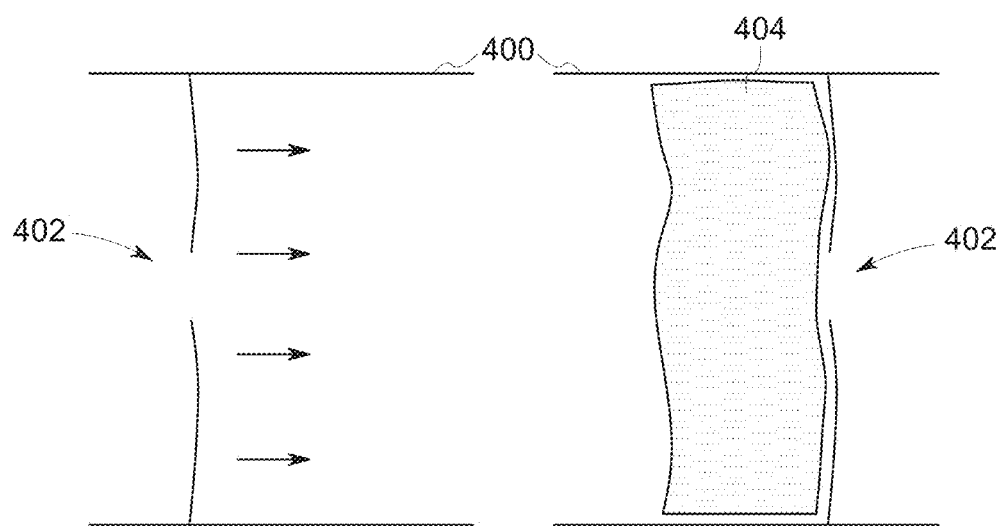
FIG. 13 depicts a closed valve after and prior to an opening event, in accordance with aspects of the present disclosure.

(B) Estimate Valve Speed From Valve Opening and Closing to Estimate the Blood Flow Rate—In a second cardiac dynamics implementation, certain properties associated with cardiac mechanics may be leveraged to calculate flow parameters. For example, as the heart beats, the aortic and mitral valve planes may move substantially though the apex of the heart stays nearly fixed (i.e., substantially stationary in relation). The volume of blood within the heart chambers of the heart is substantially constant since blood tends to flow into one chamber (e.g., the left atrium) at the same time that it is flowing out of another (e.g., the left ventricle). In this way, the plane of the respective valve 402 (FIG. 13) acts somewhat like a syringe when closed, pushing a certain volume of blood 404 along during each beat. This volume may be computed using image data by tracking the position of the valve 402 from the moment it closes (leftmost figure of FIG. 13) until the moment it opens again (rightmost figure of FIG. 13, showing the volume of blood 404 awaiting release). That is, based on the generally stable mechanics of cardiac pumping, determining the time of valve closure to the time of valve opening using tracked positions of the valve as ascertained from image data may allow blood flow to be estimated.

(C) Estimate Ventricular Blood Volume from Projection Images at Two or More Cardiac Phases to Determine Cardiac Output—In a further cardiac dynamics approach to estimate coronary flow and/or fractional flow reserve, left ventricular blood volume at one or more time points is measured from CTA images in which the blood pool within the ventricle is contrast (e.g., iodine) enhanced. By way of example, this can be done through a collection of one or more projection images comprising the entire heart, acquired at one or more time points during the cardiac cycle. The lateral extent of the projection of the ventricle may be visible in each of the projection images. By acquiring projection data at multiple view angles, the ventricular volume may be estimated at one or more time points in the cardiac cycle. The difference in ventricular blood volume between two adjacent time points divided by the time interval between these adjacent points gives the volume flow rate out of the aortic valve over this interval. This volume flow rate can then be imposed as a boundary condition at the ascending aorta inlet in a 1D coronary circulation model.

Figure 14:
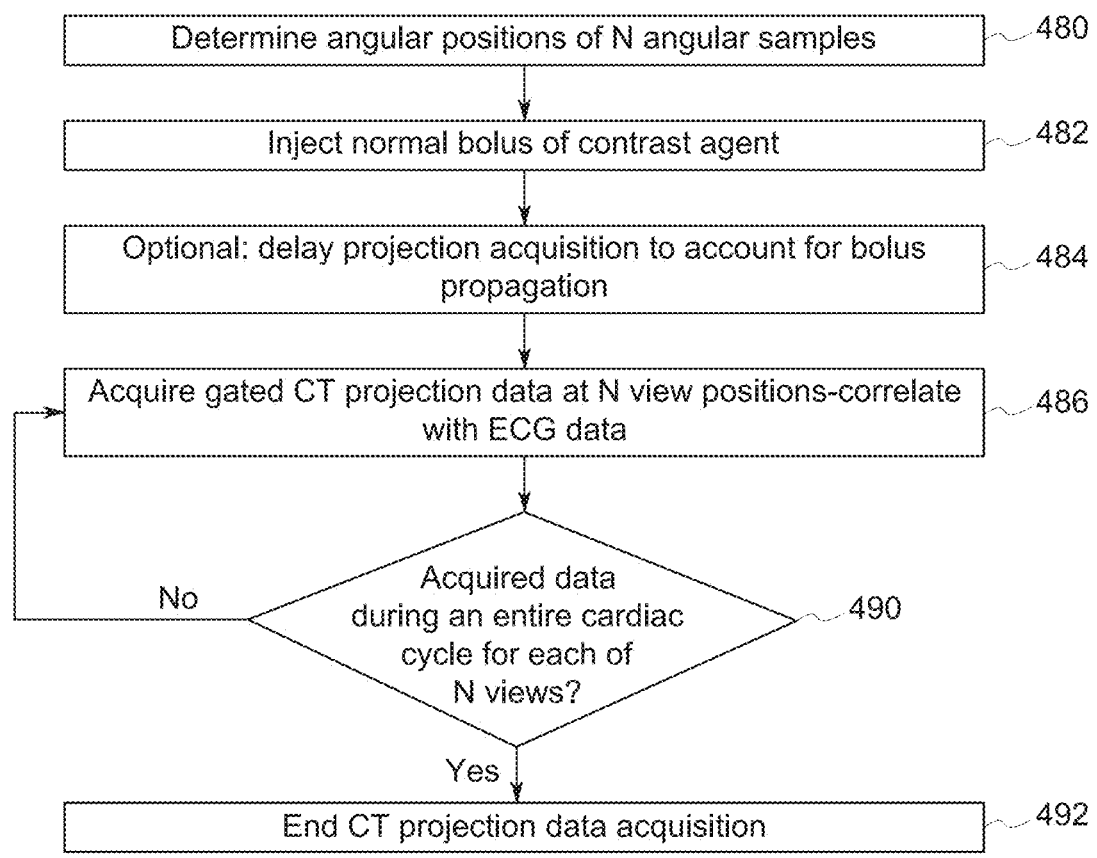
FIG. 14 depicts a process flow for CT projection data acquisition, in accordance with aspects of the present disclosure.
Figure 15:
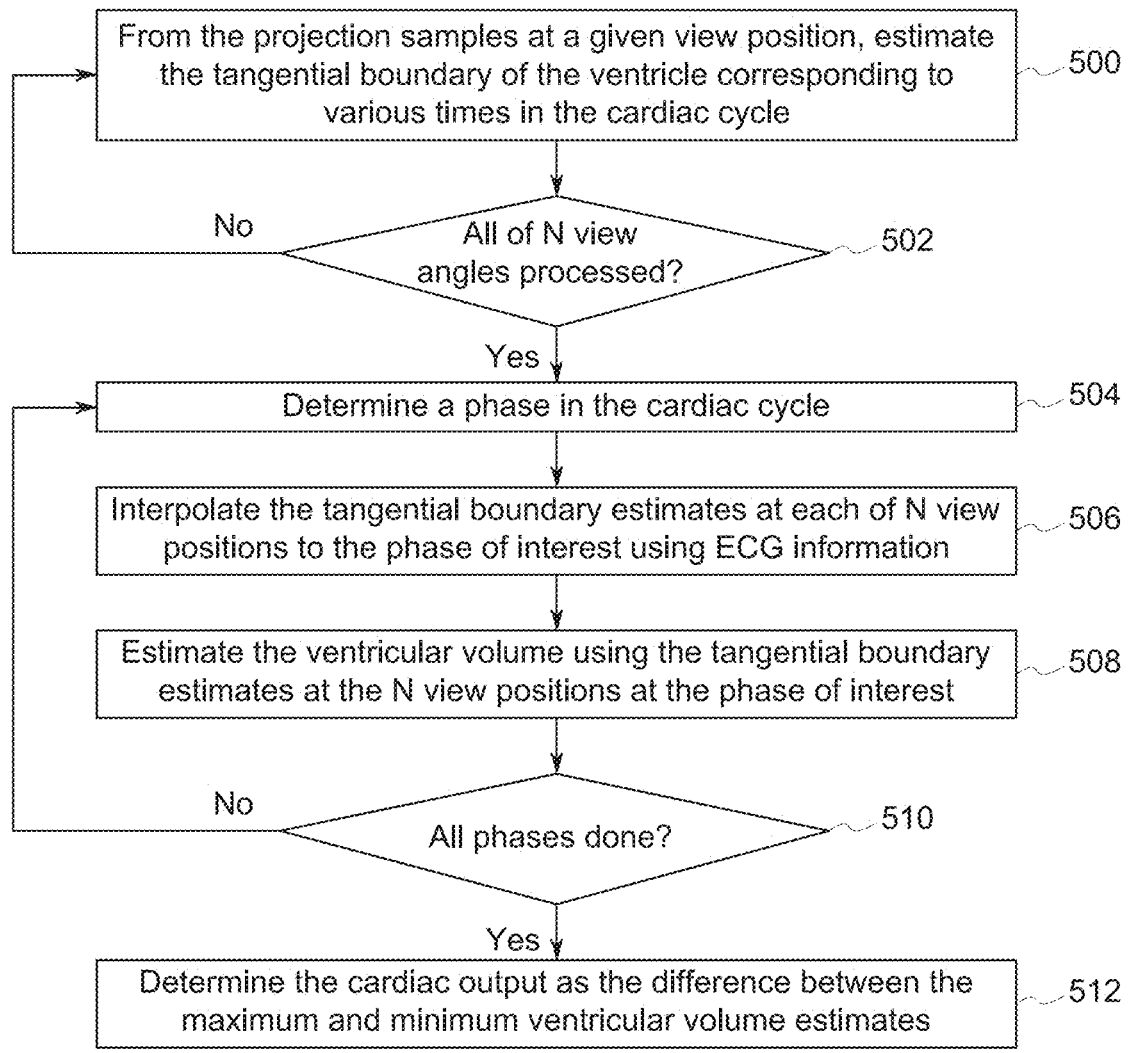
FIG. 15 depicts a process flow for CT projection data processing, in accordance with aspects of the present disclosure.

With this in mind, FIGS. 14 and 15 depict flow charts explaining aspects of such an implementation, with FIG. 14 describing steps in a data acquisition and FIG. 15 describing steps in processing the data in such an implementation.

Turning to FIG. 14, in this example, the angular positions of N angular samples is initially determined (block 480). A bolus of contrast agent is administered (block 482) to the subject. An option delay (block 484) may be provided to account for the time it takes for the contrast to propagate from the administration site to the region of interest. Once the contrast bolus is present in the region of interest (e.g., the heart chambers and coronary vasculature) CT projection data is acquired (block 486) over the N view positions. In one implementation, the acquisition of the CT projection data is concurrent with separately acquired ECG data. A determination is made (decision block 490) as to whether projection data has been acquired during an entire cardiac cycle for each of the N views. If not, the acquisition of CT projection data continues until data is acquired for the entire cardiac cycle at each of the N views. If yes, projection data acquisition is ended (block 492).

Once the acquisition process of FIG. 14 is complete, processing of the projection data may be performed, as outlined in FIG. 15. In this example, the tangential boundary of the ventricle corresponding to various times in the cardiac cycle is estimated (block 500) using the projection samples associated with a given view position. Once all view angles are processed (block 502) a phase in the cardiac cycle is determined (block 504). The tangential boundary estimates at each of the N view positions is interpolated (block 506) to the phase of interest using the correlated ECG information. The ventricular volume is then estimated (block 508) using the tangential boundary estimates at the N view positions at the phase of interest. Once all phases are processed (block 510), the cardiac output is determined (block 512) as the difference between the maximum and minimum ventricular volume estimates.

(3) Vessel Dynamics—With respect to a third set of approaches to be discussed, the properties and/or dynamics of the imaged coronary vessels are determined and used to estimate coronary flow and/or fractional flow reserve.

(A) Determine changes in cross-sectional area (with assumed stiffness)—In a first approach in which vessel dynamics is used to determine coronary flow, CT projection data or a combination of CT projection data and images are used to determine changes in vessel cross-sectional area. With assumed vessel wall stiffness, the cross-sectional area can be used to tune a 1D coronary circulation model to determine coronary flow.

For example a linear elastic model may be used to model vessel wall behavior in accordance with:

$$p - p_0 = \frac{\rho c_0^2}{A_0}(A - A_0) \quad (9)$$

where $p_0$ and $A_0$ are the reference pressure and cross-sectional area respectively. For example, $A_0$ may be the cross-sectional area obtained from CTA images at a specific cardiac phase and $p_0$ may be the corresponding pressure. In this example, $C_0$ is the pulse wave velocity, which is indicative of vessel stiffness. In one implementation, $C_0$ is unknown and typical values for pulse wave velocity in the coronary arteries are assumed. In another implementation, it is also determined from cross-sectional area changes as described below. In accordance with this approach, $p_0$ can be determined from the 1D model by assigning any difference between the predicted value of A (at the cardiac phase at which $A_0$ was obtained) and $A_0$ as $$p_0 = \frac{\rho c_0^2}{A_0}(A^{predicted} - A_0).$$

Figure 16:
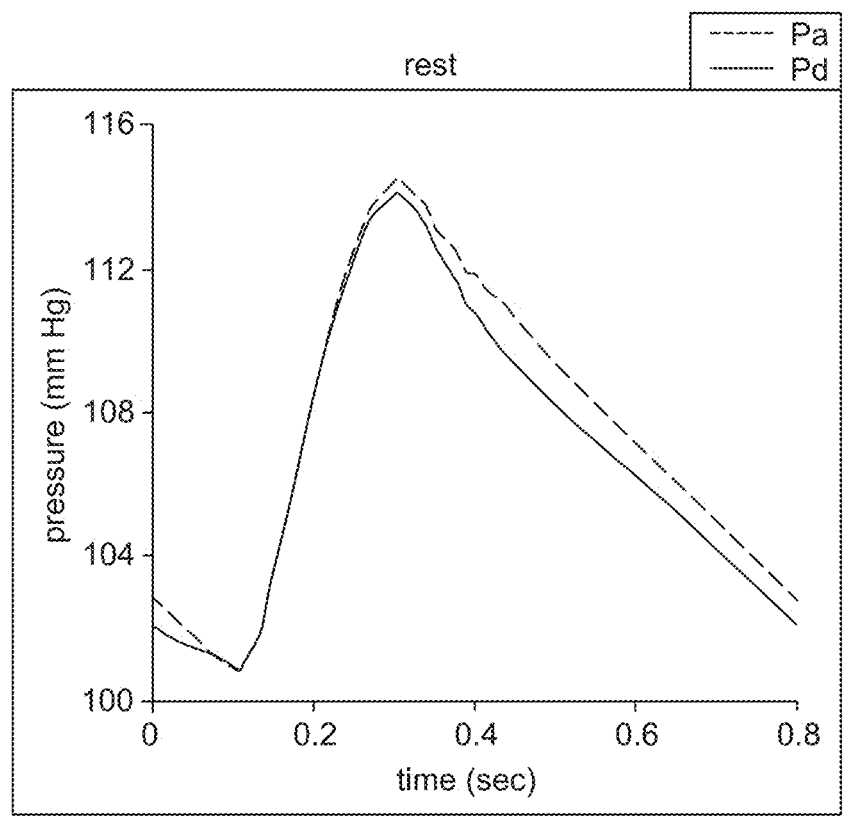
FIG. 16 graphically depicts proximal and distal pressure in a vessel with stenosis under rest conditions, in accordance with aspects of the present disclosure.
Figure 17:
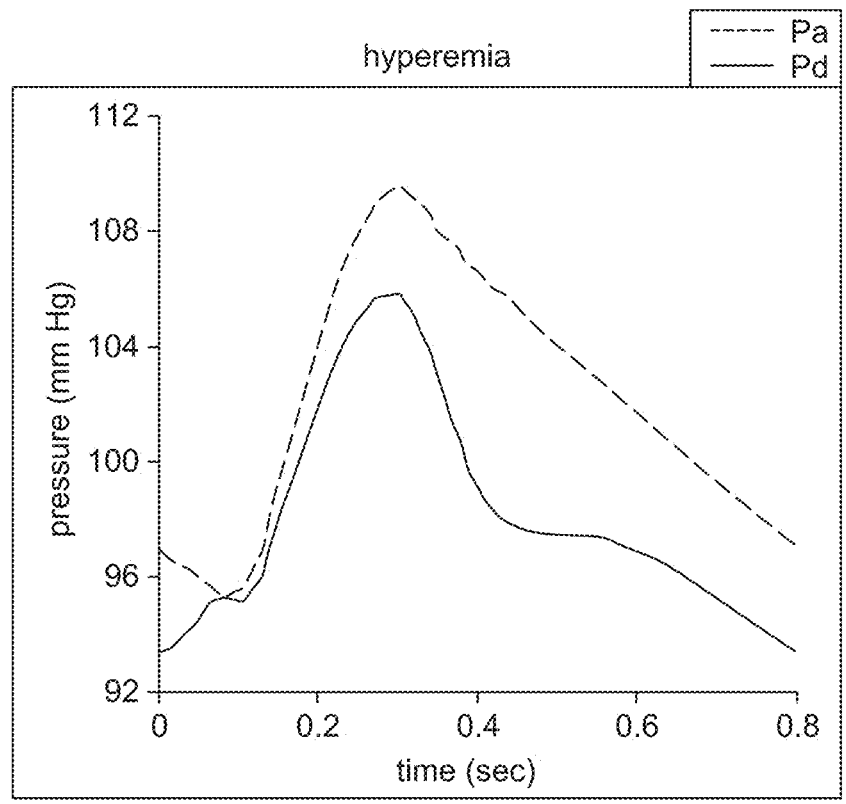
FIG. 17 graphically depicts proximal and distal pressure in a vessel with stenosis under hyperemic conditions, in accordance with aspects of the present disclosure.

The drop in pressure in a vessel segment (with or without stenosis) is related to the flow rate in that vessel segment. To illustrate this concept, FIGS. 16 and 17 show the proximal and distal pressures in a vessel segment with stenosis under rest (FIG. 16) and under hyperemic conditions (FIG. 17).

Due to the flow in the coronary arteries being diastole-dominated, a larger drop in pressure can be seen during this period at rest and this effect is accentuated under hyperemia as the flow rate is increased. Since pressure determines cross-sectional area according to the linear elastic model, cross-sectional areas determined from CTA images may be used to tune flow rate in the 1D model.

By way of example, in the present approach CT projection data or a combination of CT projection data and images are used to determine vessel cross-sectional area in one or more vessel segments at two or more cardiac phases. The data acquired at one cardiac phase can correspond to $A_0$ in the linear elastic model. The data acquired at the second cardiac phase is then used to tune flow rate in the corresponding vessel segment until the predicted and measured cross-sectional areas match within a specified tolerance, thus providing an estimate of the flow rate. The two cardiac phases can, in one implementation, correspond to the time instances at which pressure is maximum and minimum.

In one embodiment, $C_0$ in the pressure-area relationship can also be determined from cross-sectional area changes. First, the vessel elasticity is assumed to be a function of ascending aorta and coronary artery radii and given by:

$$\frac{Eh}{r} = k_1 \exp(k_2 r) + k_3 \quad (10)$$

where E is the modulus of elasticity, h is the vessel wall thickness and $k_1$, $k_2$, $k_3$ are constants. r is the radius of the ascending aorta or the coronary arteries. The vessel elasticity E is related to the pulse wave speed $C_0$ through the following equations:

$$C_0^2 = \frac{\beta}{2\rho\sqrt{A_0}} \quad (11)$$

$$\beta = \frac{\sqrt{\pi} hE}{1 - \theta^2} \quad (12)$$

Here, $\rho$ is the density of blood, $A_0$ is the cross-sectional area obtained from the CTA images at one cardiac phase, E is the modulus of elasticity, h is the vessel wall thickness and $\theta$ is the Poisson ratio. In this approach, the ascending aorta cross-sectional area at two or more cardiac phases is acquired in addition to acquisition of the coronary vessel segments at multiple cardiac phases. Cardiac output is determined from left ventricular volume changes as described previously. As in the case of coronaries, the cross-sectional area of the ascending aorta acquired at one cardiac phase can correspond to $A_0$ in the pressure-area relationship. The cross-sectional area obtained at the second cardiac phase can be used to tune the constants $k_1$, $k_2$, $k_3$ until the predicted and measured ascending aorta cross-sectional areas match within a specified tolerance.

(B) Determine changes in cross-sectional area (at rest and stress (i.e. during hyperemia or vasodilation)—In a second approach in which vessel dynamics is used to determine coronary flow, CT projection data or a combination of CT projection data and images are used to determine changes in vessel cross-sectional area. In this approach the 1D model may be tuned to determine coronary flow using a hyperemia model.

The present approach may utilize the linear elastic model and context described in the preceding approach. However, in this approach CT projection data or a combination of CT projection data and images are used to determine vessel cross-sectional area in one or more vessel segments at a single cardiac phase during rest as well as during hyperemia. In this context, the data acquired during rest can correspond to $A_0$ in the linear elastic model. The data acquired during hyperemia can then be used to tune flow rate in the corresponding vessel segment until the predicted and measured cross-sectional areas match. In this approach, a micro circulation model for hyperemia is also employed. The pulse wave velocity, $C_0$, can be assumed or determined from cross-sectional area changes as described before. For the latter case, the ascending aorta cross-sectional area would be obtained at a single cardiac phase during rest and hyperemia. The data acquired during rest can correspond to $A_0$ while the data acquired during hyperemia will be used to tune the constants $k_1$, $k_2$ and $k_3$.

(C) Determine changes in cross-sectional area upstream and downstream of a stenosis—In a third approach in which vessel dynamics is used to assess aspects of coronary flow, CT projection data or a combination of CT projection data and images are used to determine changes in vessel cross-sectional area upstream and downstream of a stenosis between high and low pressures.

In this approach the cross-sectional area differences may be used to directly infer the pressures. For example, by imaging at end-systole, the flow in the coronaries is low, so the pressure both proximal and distal to a stenosis will be very similar, i.e., $p_{P,S}=p_{D,S}$, where the first subscript denotes proximal or distal position, and the second subscript denotes diastole or systole. Thus, at these cardiac phases, reference cross-section areas both distal and proximal to the stenosis may be determined. Images may then be acquired at end-diastole, where the coronary flow is maximum. Assuming that vessel compliance both proximal and distal to the stenosis is comparable and can be estimated, the cross-sectional area difference both proximal and distal to the stenosis can be estimated. From these estimated area differences, the pressure difference at locations proximal and distal to the stenosis can in turn be estimated.

With the preceding in mind, the following equations relate the relevant mathematical relationships:

$$p_{P,D} - p_{P,S} = \frac{\rho c_0^2}{A_{P,S}}(A_{P,D} - A_{P,S}) \tag{13}$$

$$p_{D,D} - p_{D,S} = \frac{\rho c_0^2}{A_{D,S}}(A_{D,D} - A_{D,S}) \tag{14}$$

Here, $p_{P,D}$ and $p_{D,D}$ are the pressures proximal and distal to the stenosis at diastole, $p_{P,S}$ and $p_{D,S}$ are the pressures proximal and distal to the stenosis at systole, $A_{P,D}$ and $A_{D,D}$ are the cross-sectional areas proximal and distal to the stenosis at diastole, $A_{P,S}$ and $A_{D,S}$ are the cross-sectional areas proximal and distal to the stenosis at systole and $c_0$ is the pulse wave speed. By subtracting the two above equations, the pressure drop at end diastole across a stenosis can be obtained.

In addition, the absolute pressure both distal and proximal to the stenosis can be estimated and used to directly estimate fractional flow reserve once the proximal diastolic pressure is known. By subtracting the pressure area relationship upstream and downstream of the stenosis the following relationship is derived:

$$p_{P,D} - p_{D,D} = \frac{\rho c_0^2}{A_{P,S}}(A_{P,D} - A_{P,S}) - \frac{\rho c_0^2}{A_{D,S}}(A_{D,D} - A_{D,S}) \tag{15}$$

All terms on the right hand side are known assuming the pulse wave speed $C_0$ can be estimated. Once $p_{D,D}$ or $p_{P,D}$ is known, the absolute pressures upstream and downstream of the stenosis can be determined. In one implementation, the proximal diastolic pressure, $p_{P,D}$, can be estimated as follows. If the cross-sectional area proximal to the stenosis is known throughout the cardiac cycle, then the average cross-sectional area, $\overline{A}$, proximal to the stenosis can be determined. In addition, if there is not a substantial drop in mean pressure up to the proximal location, then the mean pressure at the proximal location can be assumed to be the same as the mean brachial pressure which can be determined from cuff measurements. The proximal diastolic pressure can then be determined from the following equation:

$$p_{P,D} - \overline{p} = \frac{\rho c_0^2}{\overline{A}}(A_{P,D} - \overline{A}). \tag{16}$$

With $p_{P,D}$ and $p_{D,D}$ now known, their ratio can be computed to give the fractional flow reserve value at end diastole.

In another implementation, the proximal pressure at diastole, $p_{P,D}$ is determined from the brachial cuff measurements using a population-based transfer function that relates the brachial diastolic pressure to $p_{P,D}$. Once $p_{P,D}$ is known, $p_{D,D}$ can be determined from:

$$p_{D,D} = p_{P,D} - \frac{\rho c_0^2}{A_{P,S}}(A_{P,D} - A_{P,S}) + \frac{\rho c_0^2}{A_{D,S}}(A_{D,D} - A_{D,S}) \tag{17}$$

The fractional flow reserve at end diastole can be computed as before with knowledge of $p_{P,D}$ and $p_{D,D}$.

(4) Ultrasound—With respect to a fourth set of approaches to be discussed, flow is determined using ultrasound techniques and used to tune a 1D circulation model. By way of example, trans-thoracic Doppler ultrasound may be used to determine resting or hyperemic coronary flow in a coronary artery, i.e., the left anterior descending artery. The acquired velocity or flow can be used to tune a 1D coronary circulation model as described below.

In the 1D model, the lumped model resistance for each terminal coronary vessel segment is determined using Murray's law:

$$R_i = \frac{MAP}{Q_i} = MAP \cdot \frac{\sum_{j=1}^{n} r_j^3}{Q_{rest} \cdot r_i^3} \tag{16}$$

where MAP is the mean arterial pressure, $r_i$ and $r_j$ are the radii of the terminal vessel segments, and Q is the resting coronary flow. Mean arterial pressure can be determined from brachial blood pressure measurements using a cuff. The vessel centerline and cross-sectional area may be extracted from CTA images and the radii of the terminal vessel segments can be determined, such as based upon the extracted cross-sectional areas. In practice, however, the resting coronary flow is unknown and may be determined or estimated using Doppler ultrasound measurements in this approach.

Assuming an initial resting coronary flow, the terminal segment resistances of the model can be adjusted (which is equivalent to adjusting flow rate) until the predicted average velocity within a coronary artery segment matches the measured average velocity in the same segment, as determined using ultrasound, within a specified tolerance. Since Doppler ultrasound records velocities as a function of time, the readings could also be used to adjust lumped model compliance values. Without any measurements, the compliances in the 1D model are determined so as to give physiologically realistic flow waveforms in the coronary arteries. A set time constant value, equal to the product of coronary microcirculation resistance and compliance, may be used for all the terminal vessel segments. Once the lumped resistance of the terminal segment is known, the lumped coronary artery compliance can be determined.

In addition, the ratio of myocardial compliance to coronary artery compliance may be specified to be the same for the left coronary tree terminal vessel segments so that once the lumped coronary artery compliance is known, the myocardial compliance can be determined. With knowledge of the velocity waveform in a vessel segment, both the coronary artery and myocardial compliance values can be adjusted (equivalent to tuning time constant and compliance ratio), in addition to the terminal resistance. The terminal resistance may be adjusted as before to match average velocities while the time constant and compliance ratio may be adjusted to match the velocity waveform shape.

Technical effects of the invention include estimating one or both of coronary flow or fractional flow reserve using contrast dynamics (as determined from image or CT projection data), cardiac dynamics (as determined from image or CT projection data); coronary vessel dynamics (as determined from image or CT projection data), and/or ultrasound derived coronary flow parameters used to tune a suitable coronary model.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for generating a patient-specific coronary flow model, comprising:
    acquiring or generating contrast-enhanced images of a coronary vasculature at one or more cardiac phases, wherein the coronary vasculature comprises one or more vessel segments of interest;
    analyzing the contrast-enhanced images to determine spatial contrast agent concentration distribution in each vessel segment of interest;
    accessing a generalized coronary model that models a coronary vasculature comprising at least each vessel segment of interest, wherein the generalized coronary model is parameterized by one or more parameters; and
    tuning the one or more parameters of the generalized coronary model to generate a patient-specific coronary flow model that replicates the spatial contrast agent concentration distribution in each vessel segment of interest as observed in the contrast-enhanced images.

2. The method of claim 1, wherein acquiring contrast-enhanced images comprises performing a computed tomography angiography scan or an X-ray angiography scan.

3. The method of claim 1, wherein determining the spatial contrast agent concentration distribution comprises determining an average opacification at one or more points in each vessel segment of interest.

4. The method of claim 1, wherein analyzing the contrast-enhanced images comprises determining a vessel centerline and cross-sectional area for the vessel segments of interest.

5. The method of claim 1, wherein the contrast-enhanced images are acquired following administration of a patterned bolus of contrast agent, wherein the patterned bolus comprises one or more contrast intervals interleaved with a respective low or no contrast interval, wherein the contrast intervals are characterized by higher concentrations of the contrast agent than the respective low or no contrast interval.

6. The method of claim 1, wherein the generalized coronary model comprises a 1D wave propagation model for vessels coupled to lumped parameter models for one or more of the heart, systemic circulation, and coronary microcirculation and wherein the one or more tuned parameters correspond to lumped model parameters for the coronary microcirculation.

7. The method of claim 1, wherein tuning the one or more parameters comprises minimizing the difference between contrast agent opacification spatial distribution obtained from images and a predicted contrast agent opacification spatial distribution averaged over the scan duration.

8. The method of claim 7, wherein the predicted contrast opacification spatial distribution is generated by solving a contrast-agent propagation model in conjunction with the generalized coronary model.

9. The method of claim 8, wherein the contrast-agent propagation model uses a time variation of contrast agent opacification in the ascending aorta as an inlet boundary condition.

10. The method of claim 9, wherein the time variation of contrast agent opacification is obtained from a scan separate from a diagnostic scan, wherein a first radiation dose utilized in obtaining the scan is lower than a second radiation dose utilized in obtaining the diagnostic scan.

11. The method of claim 1, wherein the patient-specific coronary flow model is used to compute a pressure distribution and to estimate fractional flow reserve within the one or more vessel segments of interest.

12. The method of claim 1, wherein the patient-specific coronary flow model is used to estimate fractional flow reserve for one or more lesions in the coronary vasculature.

13. The method of claim 12, wherein the one or more lesions comprises one or more stenosis or narrowings in the coronary vasculature.

14. A method for generating a patient-specific coronary flow model, comprising:
    acquiring or generating contrast-enhanced images of a coronary vasculature at one or more cardiac phases, wherein the coronary vasculature comprises one or more vessel segments of interest;
    analyzing the contrast-enhanced images to determine spatial contrast agent concentration distribution in each vessel segment of interest;
    accessing a generalized coronary model that models a coronary vasculature comprising at least each vessel segment of interest, wherein the generalized coronary model is parameterized by one or more parameters; and
    tuning the one or more parameters of the generalized coronary model to generate a patient-specific coronary flow model that replicates the spatial contrast agent concentration distribution in each vessel segment of interest as observed in the contrast-enhanced images;
    wherein the contrast-enhanced images are acquired following administration of a patterned bolus of contrast agent, wherein the patterned bolus comprises one or more contrast intervals interleaved with a respective low or no contrast interval, wherein the contrast intervals are characterized by higher concentrations of the contrast agent than the respective low or no contrast interval.

* * * * *